United States Patent
Connor et al.

(10) Patent No.: US 6,525,233 B1
(45) Date of Patent: Feb. 25, 2003

(54) PROCESS FOR PREPARING A MODIFIED ALKYLARYL

(75) Inventors: Daniel Stedman Connor, Cincinnati, OH (US); Jeffrey John Scheibel, Loveland, OH (US); James Charles Theophile Roger Burkett-St. Laurent, Cincinnati, OH (US); Thomas Anthony Cripe, Loveland, OH (US); Kevin Lee Kott, Loveland, OH (US); Phillip Kyle Vinson, Fairfield, OH (US)

(73) Assignee: The Procter & Gamble Company, Cincinnati, OK (US)

( * ) Notice: Subject to any disclaimer, the term of this patent is extended or adjusted under 35 U.S.C. 154(b) by 0 days.

(21) Appl. No.: 09/479,364

(22) Filed: Jan. 7, 2000

Related U.S. Application Data

(63) Continuation of application No. PCT/IB98/16362, filed on Aug. 4, 1998.
(60) Provisional application No. 60/055,437, filed on Aug. 8, 1997.

(51) Int. Cl.$^7$ .............................. C07C 2/64; C07C 2/66
(52) U.S. Cl. ...................... 585/448; 585/455; 585/323
(58) Field of Search ................................ 585/448, 455, 585/323, 820, 822

(56) References Cited

U.S. PATENT DOCUMENTS

| | | | |
|---|---|---|---|
| 2,477,382 A | | 7/1949 | Lewis ..................... 260/671 |
| 2,564,072 A | | 8/1951 | Lien et al. .................. 260/671 |
| 2,909,574 A | * | 10/1959 | Woodle ...................... 585/448 |
| 2,985,589 A | * | 5/1961 | Broughton et al. .......... 210/676 |
| 3,196,174 A | | 7/1965 | Cohen ........................ 260/505 |
| 3,238,249 A | | 3/1966 | Mirviss et al. .............. 260/505 |
| 3,312,745 A | | 4/1967 | Habeshaw et al. .......... 260/638 |
| 3,333,014 A | * | 7/1967 | Adams et al. ............... 585/315 |
| 3,341,614 A | | 9/1967 | Wirth et al. ................. 260/671 |
| 3,351,654 A | | 11/1967 | Gudelis ...................... 260/505 |
| 3,355,484 A | | 11/1967 | Bloch ........................ 260/505 |
| 3,413,373 A | * | 11/1968 | Bloch ........................ 585/315 |
| 3,427,342 A | | 2/1969 | Brooks et al. .............. 260/458 |
| 3,442,964 A | | 5/1969 | Oldham ...................... 260/671 |
| 3,442,965 A | | 5/1969 | Oldham ...................... 260/671 |
| 3,491,030 A | | 1/1970 | Fields ........................ 252/161 |
| 3,492,364 A | | 1/1970 | Jones et al. ................. 260/671 |
| 3,562,797 A | | 2/1971 | Hu .......................... 260/683.3 |
| 3,674,885 A | | 7/1972 | Griessinger et al. ........ 260/671 |
| 4,235,810 A | | 11/1980 | Osselet et al. ............. 260/505 |
| 4,259,193 A | | 3/1981 | Tirtiaux et al. .............. 252/33 |
| 4,301,316 A | | 11/1981 | Young ....................... 585/455 |
| 4,301,317 A | | 11/1981 | Young ....................... 585/455 |
| 4,447,664 A | | 5/1984 | Murchison et al. ......... 585/323 |
| 4,533,651 A | | 8/1985 | Masters et al. ............. 502/117 |
| 4,587,374 A | | 5/1986 | Peters ....................... 585/670 |
| 4,645,623 A | | 2/1987 | Dolan et al. ................ 252/558 |
| 4,731,497 A | | 3/1988 | Grey ......................... 585/455 |
| 4,855,527 A | | 8/1989 | Page et al. .................. 585/527 |
| 4,870,038 A | | 9/1989 | Page et al. ................... 502/62 |

(List continued on next page.)

FOREIGN PATENT DOCUMENTS

| | | | |
|---|---|---|---|
| AU | 39394/89 | 2/1990 | ........... C07C/02/02 |
| CA | 2201953 | 10/1997 | ............ C07C/5/27 |
| DE | 0 559 510 | 2/1993 | |
| DE | 42 24 947 | 2/1994 | .......... C11D/3/386 |
| DE | 42 36 698 | 2/1994 | .......... C11D/3/386 |
| EP | 0 321 177 | 6/1989 | ........... C01B/33/34 |
| EP | 0 364 012 | 4/1990 | ......... C07C/303/24 |
| EP | 0 466558 | 1/1992 | ......... C07C/15/107 |
| EP | 0 469 940 | 2/1992 | ......... C07C/15/107 |
| EP | 0 807 616 | 11/1997 | ............ C07C/2/70 |
| FR | 2697246 | 4/1994 | ......... C07C/15/107 |
| GB | 936 882 | 9/1963 | |
| GB | 2 083 490 | 3/1982 | |
| GB | 2 278 125 | 11/1994 | ............ C11D/1/12 |
| SU | 793972 | 1/1981 | ............ C07C/2/22 |
| WO | WO 88/07030 | 9/1988 | ............ C07C/2/32 |
| WO | WO 95/17961 | 7/1995 | ............ B01J/29/06 |
| WO | WO 95/18084 | 7/1995 | ............ C07C/5/27 |
| WO | WO 95/21225 | 8/1995 | ............ C09K/7/00 |
| WO | WO 97/01521 | 1/1997 | ............ C07C/1/04 |
| WO | WO 97/29063 | 8/1997 | ......... C07C/15/107 |
| WO | WO 97/29064 | 8/1997 | ......... C07C/15/107 |

OTHER PUBLICATIONS

"Petroleum–Based Raw Materials for Anionic Surfactants", *Surfactant Science Series*, vol. 7, Part 1, Chapter 2, pp. 11–86, Ed. W. M. Linfield, Marcel Dekker, Inc., New York (1996).

Nooi, J. R., et al., "Isomerization Reactions Occuring on Alkylation of Benzene with Some Branched Long–Chain 1–Alkenes", *Recueil*, vol. 88, No. 4, pp. 398–410 (1969).

Research Disclosure No. 41412, "Hydrocarbon Mixture", *Research Disclosure*, vol. 414 (Oct. 1998).

*Primary Examiner*—Walter D. Griffin
(74) *Attorney, Agent, or Firm*—Ian S. Robinson; C. Brant Cook; Kim W. Zerby

(57) ABSTRACT

Processes for making particularly branched, especially monomethyl-branched or nongeminal dimethyl-branched surfactants used in cleaning products; preferred processes comprising particular combinations of two or more adsorptive separation steps and, more preferably, particular alkylation steps; products of such processes, including certain modified alkylbenzenes, modified alkylbenzenesulfonate surfactants, and consumer cleaning products, especially laundry detergents, containing them. Preferred processes herein more specifically use specific, unconventional sequences of sorptive separation steps to secure certain branched hydrocarbon fractions which are used in further process steps as alkylating agents for arenes or for other useful surfactant-making purposes. Surprisingly, such fractions can even be derived from effluents from current linear alkylbenzene manufacture.

33 Claims, 8 Drawing Sheets

U.S. PATENT DOCUMENTS

| | | | |
|---|---|---|---|
| 4,959,491 A | 9/1990 | Threlkel | 562/94 |
| 4,962,256 A | 10/1990 | Le et al. | 585/467 |
| 4,973,788 A | 11/1990 | Lin et al. | 585/511 |
| 4,990,718 A | 2/1991 | Pelrine | 585/455 |
| 4,996,386 A | 2/1991 | Hamilton, Jr. et al. | 585/646 |
| 5,012,021 A * | 4/1991 | Vora et al. | 585/315 |
| 5,026,933 A | 6/1991 | Blain et al. | 585/7 |
| 5,030,785 A | 7/1991 | Huss, Jr. et al. | 585/456 |
| 5,087,788 A | 2/1992 | Wu | 585/512 |
| 5,146,026 A | 9/1992 | Berna Tejero et al. | 585/467 |
| 5,177,280 A | 1/1993 | Juguin et al. | 585/323 |
| 5,196,574 A | 3/1993 | Kocal | 562/94 |
| 5,196,624 A | 3/1993 | Threlkel et al. | 585/513 |
| 5,196,625 A | 3/1993 | Threkel et al. | 585/513 |
| 5,198,595 A | 3/1993 | Lee et al. | 585/467 |
| 5,210,060 A | 5/1993 | Radlowski et al. | 502/202 |
| 5,243,116 A | 9/1993 | Lee et al. | 85/467 |
| 5,245,072 A | 9/1993 | Giancobbe et al. | 560/99 |
| 5,246,566 A | 9/1993 | Miller | 208/27 |
| 5,258,566 A | 11/1993 | Kresge et al. | 585/467 |
| 5,276,231 A * | 1/1994 | Kocal et al. | 585/323 |
| 5,302,732 A | 4/1994 | Steigleder et al. | 554/98 |
| 5,326,928 A | 7/1994 | Benazzi et al. | 585/820 |
| 5,334,793 A | 8/1994 | Kocal | 585/323 |
| 5,344,997 A | 9/1994 | Kocal | 568/628 |
| 5,401,896 A | 3/1995 | Kuehl et al. | 585/455 |
| 5,491,271 A | 2/1996 | Marinangeli et al. | 585/468 |
| 5,510,306 A | 4/1996 | Murray | 502/64 |
| 5,574,198 A * | 11/1996 | Radici et al. | 585/323 |
| 5,602,292 A | 2/1997 | Perego et al. | 585/750 |
| 5,625,105 A | 4/1997 | Lin et al. | 585/511 |
| 5,811,612 A | 9/1998 | Girotti et al. | 585/467 |
| 5,811,623 A | 9/1998 | Ryu et al. | 585/671 |
| 5,922,922 A * | 7/1999 | Harris et al. | 585/323 |

* cited by examiner

PROCESS FOR PREPARING A MODIFIED ALKYLARYL

CROSS REFERENCE

This is a continuation under 35 USC §120 of PCT International Application Ser. No. PCT/IB98/16362, filed Aug. 4, 1998; which claims priority to Provisional Application Ser. No. 60/055,437, filed Aug. 8, 1997.

FIELD OF THE INVENTION

The present invention is in the field of processes for making surfactants useful in cleaning products. Preferred processes comprise particular combinations of adsorptive separation steps to separate certain hydrocarbons using specific means. Preferably these means include combinations of two or more particular adsorbent beds and two or more of particular types of rotary valves, as well as specified types of porous adsorbents having pore sizes in excess of those used in conventional linear alkylbenzene manufacture. Preferred processes further employ particular alkylation steps having specified internal isomer selectivities. The invention is also in the field of products of such processes, including certain modified alkylbenzenes, of modified alkylbenzenesulfonate surfactants, and of consumer cleaning products, especially laundry detergents, containing them. Preferred processes herein employ unconventional sequences of adsorptive separation steps to secure certain branched hydrocarbon fractions which are then used in additional process steps as alkylating agents for arenes or for other useful surfactant-making purposes. Surprisingly, such fractions can even be derived from effluents from current linear alkylbenzene manufacture.

BACKGROUND OF THE INVENTION

Historically, highly branched alkylbenzenesulfonate surfactants, such as those based on tetrapropylene (known as "ABS" or "TPBS") were used in detergents. However, these were found to be very poorly biodegradable. A long period followed of improving manufacturing processes for alkylbenzenesulfonates, making them as linear as practically possible ("LAS"). The overwhelming part of a large art of linear alkylbenzenesulfonate surfactant manufacture is directed to this objective. Large-scale commercial alkylbenzenesulfonate processes in use in the U.S. today are directed to linear alkylbenzenesulfonates. However, linear alkylbenzenesulfonates are not without limitations; for example, they would be more desirable if improved for hard water cleaning properties.

In the petroleum industry, various processes have recently been developed, for example for producing low viscosity lube oil or high-octane gasoline, which the inventors have now found provide useful new insight on how to delinearize hydrocarbons to a limited and controlled extent. Such deliberate delinearization, however, is not a feature of any current commercial processes in the different field of alkylbenzenesulfonate surfactant manufacture for consumer products. This is not surprising, in view of the overwhelming volume of LAS surfactant art teaching toward making linear compounds and away from delinearization.

The majority of commercial processes for making alkylbenzenes rely on HF or aluminum chloride catalyzed alkylation of benzene. Quite recently, it has been discovered that certain zeolite catalysts can be used for alkylation of benzene with olefins. Such a process step has been described in the context of otherwise conventional processes for manufacture of linear alkylbenzenesulfonates. For example, the DETAL® process of UOP uses a zeolite alkylation catalyst. The DETAL® process and all other current commercial processes for alkylbenzenesulfonate manufacture are believed to fail to meet the internal isomer selectivity requirements of the preferred inventive process and alkylation catalyst defined hereinafter. Moreover, the DETAL® process catalyst or catalysts are believed to lack the moderate acidity and intermediate pore size of alkylation catalysts used in the preferred processes of the present invention. Other recent literature describes the use of mordenite as an alkylation catalyst, but no such disclosure makes the combination of specific process steps required by the instant invention. Moreover, in view of the linearity desired in alkylbenzenesulfonate products of conventionally known processes, they also generally include steps directed to the provision or making of a substantially linear hydrocarbon, not a delinearized one, prior to the alkylation. Possible exceptions are in U.S. Pat. No. 5,026,933 and U.S. Pat. No. 4,990,718. These and other known processes have numerous shortcomings from the standpoint of the detergent industry in terms of cost, catalyst limitations in the propylene oligomerization or olefin dimerization stage, presence of large volumes of distillation fractions that would need to be discarded or find nondetergent customers, and limited range of product compositions, including mixtures of chainlengths attainable. Such developments by the petroleum industry are, in short, not optimal from the standpoint of the expert formulator of detergent products.

It is also known in the art to make linear alkylbenzenes using particular adsorptive separation processes. See U.S. Pat. No. 2,985,589. Such processes as described hitherto however do not provide branched alkylbenzenesulfonates.

It is also known in the art to prepare long-chained methyl paraffins for use as industrial solvents by processes which include urea clathration and separation on "molecular sieves". See Chemical Abstracts, 83:100693 and JP 49046124 B4. This process assertedly involves double urea adduction, for example treating a petroleum fraction once with urea to remove n-alkanes as complexes, and then a second time with excess urea to obtain adducts of mixed n-alkanes and long-chained monomethyl paraffins. While this process may have some limited usefulness and may be included in the overall processes of the invention as most broadly defined, its limitations are considerable. This process, despite dating from 1974, is not known to have been incorporated into any overall process for making surfactants such as the modified alkylbenzenesulfonates described herein.

BACKGROUND ART

U.S. Pat. No. 2,985,589; Chemical Abstracts, 83:100693; JP 49046124 B4 12/07/74; EP 559,510 A Sep. 8, 1993; EP 559,510 B1 Jan. 24, 1996; U.S. Pat. No. 5,026,933; U.S. Pat. No. 4,990,718; U.S. Pat. No. 4,301,316; U.S. Pat. No. 4,301,317; U.S. Pat. No. 4,855,527; U.S. Pat. No. 4,870,038; U.S. Pat. No. 2,477,382; EP 466,558, Jan. 15, 1992; EP 469,940, Feb. 5, 1992; FR 2,697,246, Apr. 29, 1994; U.S. Pat. No. 793,972, Jan. 7 1981; U.S. Pat. No. 2,564,072; U.S. Pat. No. 3,196,174; U.S. Pat. No. 3,238,249; U.S. Pat. No. 3,355,484; U.S. Pat. No. 3,442,964; U.S. Pat. No. 3,492,364; U.S. Pat. No. 4,959,491; WO 88/07030, Sep. 25, 1990; U.S. Pat. No. 4,962,256, U.S. Pat. No. 5,196,624; U.S. Pat. No. 5,196,625; EP 364,012 B, 2/15/90; U.S. Pat. No. 3,312,745; U.S. Pat. No. 3,341,614; U.S. Pat. No. 3,442,965; U.S. Pat. No. 3,674,885; U.S. Pat. No. 4,447,664; U.S. Pat. No. 4,533,651; U.S. Pat. No. 4,587,374; U.S. Pat. No. 4,996,386;

U.S. Pat. No. 5,210,060; U.S. Pat. No. 5,510,306; WO 95/17961, Jul. 6, 1995; WO 95/18084; U.S. Pat. No. 5,510, 306; U.S. Pat. Nos. 5,087,788; 4,301,316; 4,301,317; 4,855, 527; 4,870,038; 5,026,933; 5,625,105 and 4,973,788 are useful by way of background to the invention. Cited documents EP 559,510 A and B in particular relate to making high-octane gasolines by recycling streams to an isomerization reactor. Grafted porous materials of EP 559,510 and grafting of zeolites, e.g., by tin alkyls, are useful in the present invention. U.S. Pat. No. 5,107,052 likewise relates to improving octane ratings of gasoline and describes separating C4–C6 methyl paraffins using various molecular sieves such as AlPO4-5, SSZ-24, MgAPO-5 and/or MAPSO-5 containing less than 2% water. These sieves are assertedly capable of selectively adsorbing dimethyl paraffins and not adsorbing monomethyl and normal paraffins.

The manufacture of alkylbenzenesulfonate surfactants has recently been reviewed. See Vol. 56 in "Surfactant Science" series, Marcel Dekker, New York, 1996, including in particular Chapter 2 entitled "Alkylarylsulfonates: History, Manufacture, Analysis and Environmental Properties", pages 39–108 which includes 297 literature references. This work provides access to a great deal of literature describing various processes and process steps such as dehydrogenation, alkylation, alkylbenzene distillation and the like. See also "Detergent Alkylate" in Encyclopedia of Chemical Processing and Design, Eds. Mc.Ketta and Cunningham, Marcel Dekker, N.Y., 1982., especially pages 266–284. Adsorption processes such as UOP's Sorbex process and other associated processes are also described in Kirk Othmer's Encyclopedia of Chemical Technology, 4$^{th}$. Edition, Vol. 1, see "Adsorption and Liquid Separation", including pages 583–598 and references cited therein. See also publications by UOP Corp., including the "Processing Guide" available from UOP Corp., Des Plaines, Ill. Commercial paraffin isolation and separation processes using molecular sieves include MOLEX® (UOP Inc.), a liquid-phase process, and ISOSIV® (Union Carbide Corp.) as well as ENSORB® (Exxon Corp.) and TSF® or Texaco Selective Finishing process, which are vapor-phase processes. All these processes are believed to use 5 Angstrom molecular sieves as porous media. Where not noted herein, the operating temperatures, pressures and other operating conditions and apparatus for any process step are conventional, that is, as already well known and defined in the context of manufacturing linear alkylbenzenesulfonate surfactants. Documents referenced herein are incorporated in their entirety.

Solid lines are used for essential process steps and process streams. Dashed lines identify steps and streams which may not be essential in the processes as most broadly defined but which are present in various preferred process embodiments. Rounded rectangles identify process steps, stages or units. Numbered lines identify feedstocks, intermediate process streams and products. "SOR" identifies an adsorptive separation step. "4/5" identifies that the adsorptive separation uses small-pore zeolite, especially Ca zeolite 5A, which is completely conventional in linear alkylbenzene manufacture. "5/7" identifies that the adsorptive separation uses a porous material such as SAPO-11 or any equivalent porous material having the ability to adsorb monomethyl branched paraffins and/or monomethyl branched monoolefins and/or nongeminal dimethyl paraffins and/or nongeminal dimethyl olefins while rejecting geminal dimethyl hydrocarbons, cyclic (five, six or higher membered ring) hydrocarbons or higher branched hydrocarbons, whether aromatic or aliphatic. The term "geminal dimethyl" as used herein means that there are two methyls attached to an internal carbon atom of a hydrocarbon, as in:

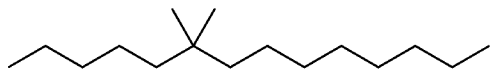

The large-pore porous materials herein should not adsorb such hydrocarbons. In contrast, the following hydrocarbons should be adsorbed. They are illustrative of what is meant by the term "nongeminal dimethyl" hydrocarbons:

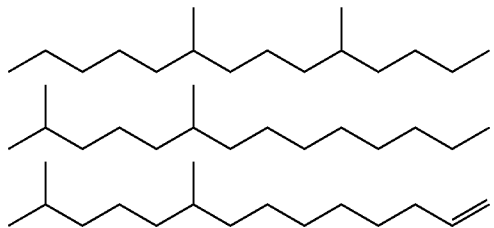

Note that any methyl moieties at the ends of the main chain are not counted in defining the term "nongeminal dimethyl" as used herein. Further, consistent with this convention, the following hydrocarbon should be adsorbed by the large-pore porous material. It is a "mononomethyl" hydrocarbon:

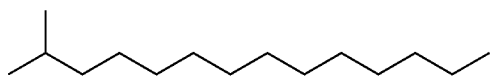

Large-pore porous materials suitable for use herein are more fully and more generally described in the specification hereinafter. "DEH" identifies a step of at least partial dehydrogenation of a stream (partial dehydrogenation being typical in conventional linear alkylbenzene manufacture though complete dehydrogenation can also be used herein), and "ALK" identifies an alkylation step. Any step, stage or unit identified by a rounded rectangle can in practice comprise only the essential step or can, more typically, include within it an additional step or steps which may be optional in the invention as most broadly defined, or which may be essential only in a preferred embodiment. Such additional steps not shown include, for example, distillation steps of types commonly practiced in the art.

Figure 1:
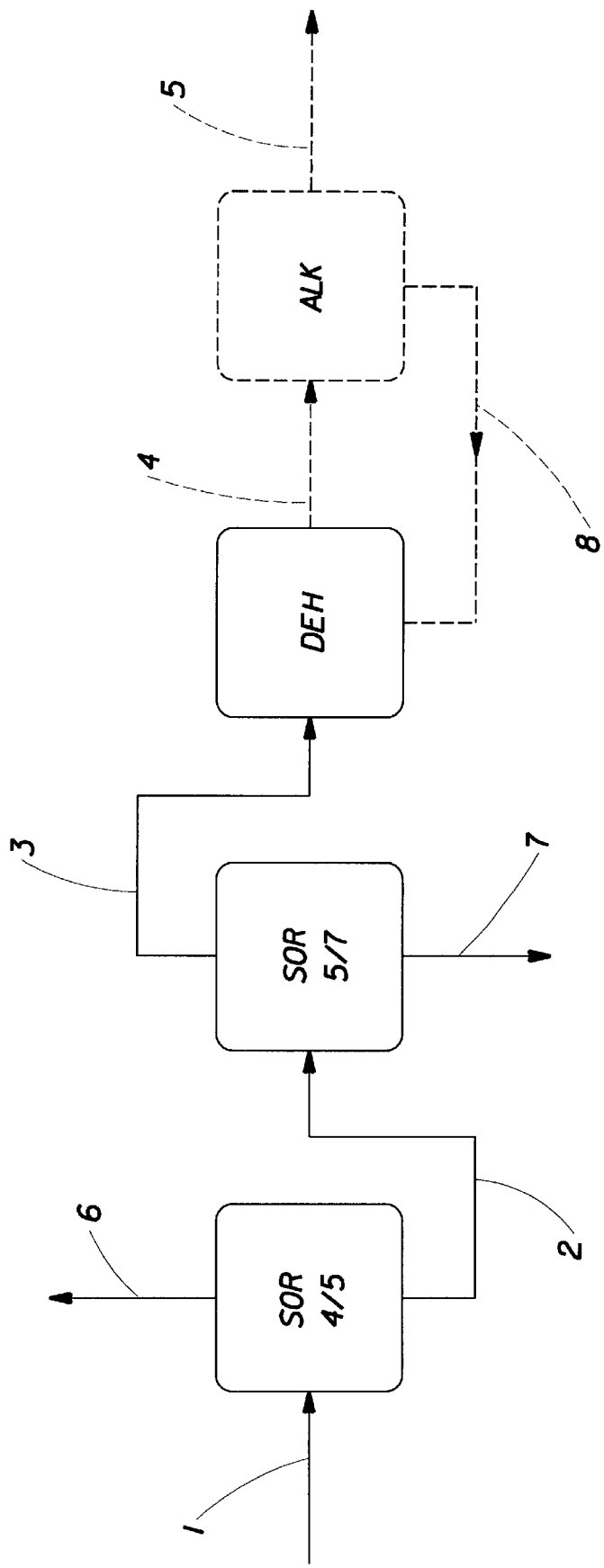
FIGS. 1–7 are schematic drawings of some processes in accordance with the invention.

With the aforementioned conventions in mind, it will be seen that FIG. 1 illustrates a process having, in sequence, two adsorptive separations, collectively in accordance with adsorptive separation stage (a) of the invention as defined hereinafter; followed by a dehydrogenation step (step (b) hereinafter); optionally followed by an alkylation step (step (c) hereinafter). While step (c) is optional in the invention as most broadly defined, it is present in all preferred embodiments which relate to making modified alkylbenzenes in accordance with the invention and, when making modified alkylbenzenesulfonate surfactants, is typically followed by (d) sulfonation, (e) neutralization and (f) mixing to formulate into a consumer cleaning product. Steps (d) though (f) use conventional means and are not explicitly shown in FIGS. 1–8.

In the FIG. 1 process, a hydrocarbon feed 1 passes to the first adsorptive separation step, for example a step in conformity with U.S. Pat. No. 2,985,589, which uses a bed of 4–5 Angstrom zeolite. A linear hydrocarbon stream is discarded as a reject stream 6. For comparison, in conventional linear alkylbenzene manufacture, stream 6, comprising a high proportion of linear hydrocarbons, would pass to DEH while step SOR 5/7 and associated streams would be absent. In the present process according to FIG. 1, an intermediate branched-enriched hydrocarbon stream is retained 2 and passes to a second adsorptive separation. The second adsorptive separation uses a particular type of porous media and produces a branched-enriched stream 3 (product of stage (a) as defined hereinafter) which passes to the dehydrogenation reactor (DEH); as well as a reject stream 7. The particular type of porous media is preferably a "large-pore" zeolite, such zeolite herein being characterized by a pore size larger than that of the zeolites used in making linear alkylbenzenes, and very preferably, a pore size of from above about 5 Angstrom to about 7 Angstrom though larger pore materials can be used and their pore sizes can be "tuned down", for example by use of tin alkyls. Stream 4 represents dehydrogenated branched-enriched hydrocarbon; stream 8 represents recycled branched paraffins. Also shown is an alkylation step according to the invention which is included in a preferred embodiment of the invention. Output from the alkylation step is a modified alkylbenzene as defined elsewhere herein.

Figure 2:
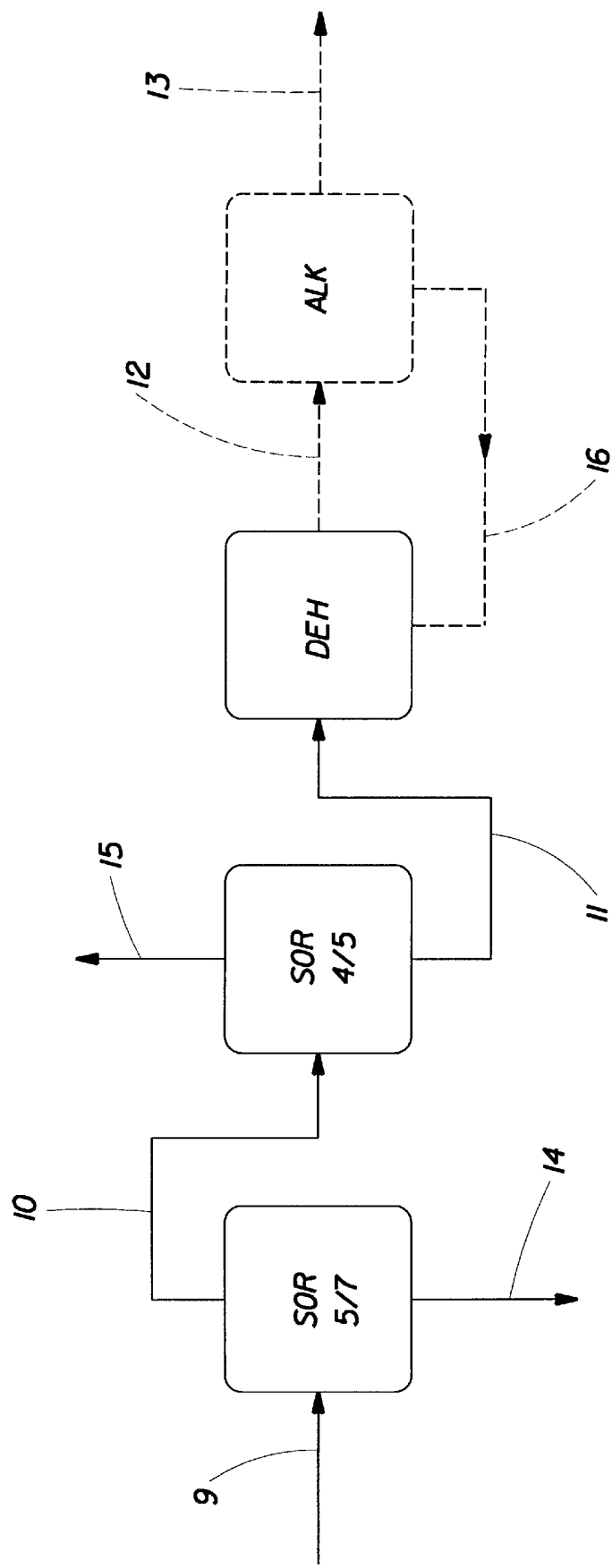

FIG. 2 is a schematic drawing identifying steps in another embodiment of the present process. While generally similar to the process of FIG. 1, the FIG. 2 process has important differences, especially in that the adsorptive separation steps are reversed with respect to pore sizes in the adsorbent beds.

Figure 4:
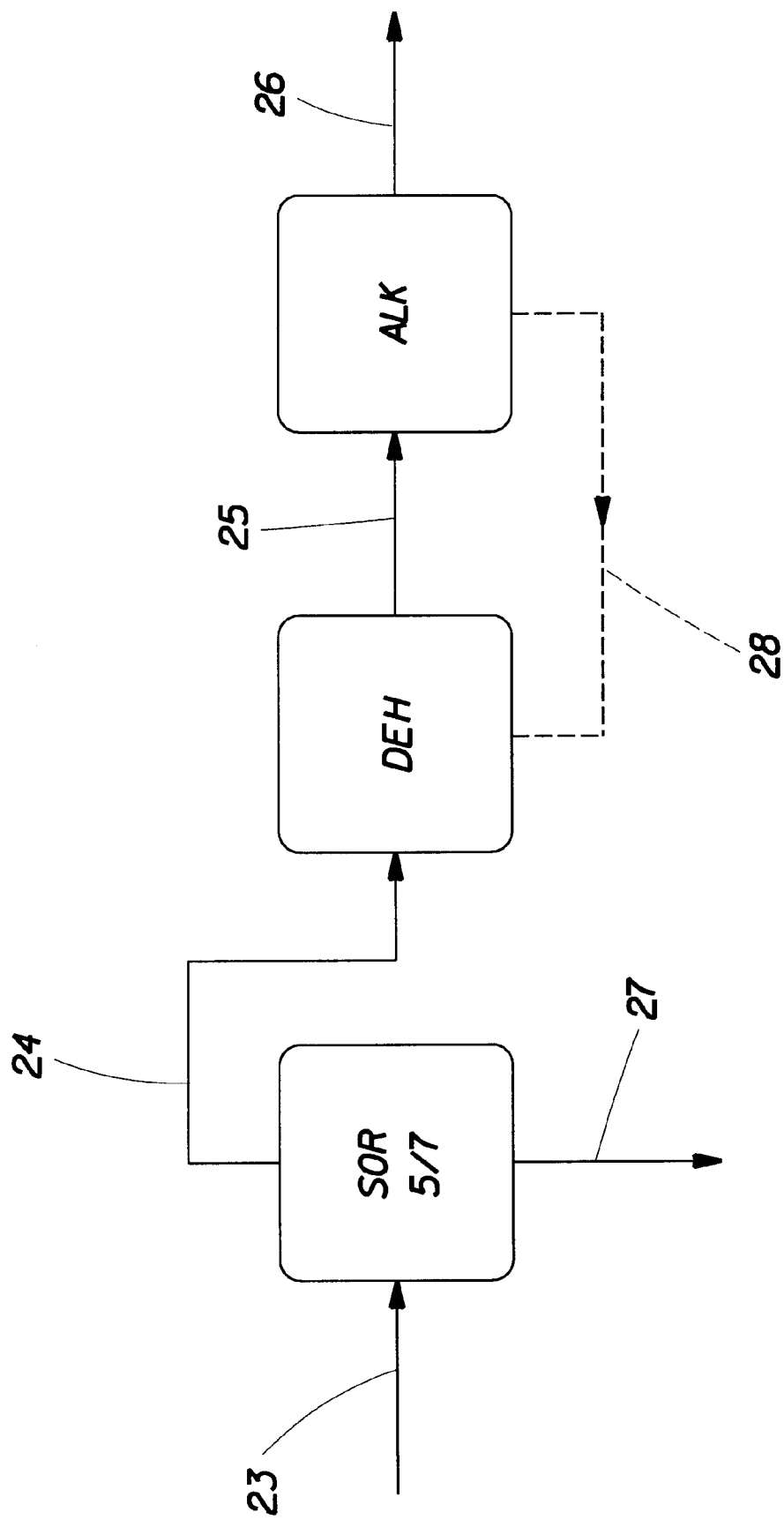

FIG. 4 is a schematic drawing identifying an embodiment of the invention which starts with a hydrocarbon feedstock 23 such as branched effluent from a conventional linear alkylbenzene manufacturing process. An adsorptive separation step using particular porous media is used to produce a reject stream 27 and a branched-enriched stream 24. The latter is dehydrogenated in the step marked DEH. The particular type of porous media is preferably a zeolite having pore size larger than that of the zeolites used in making linear alkylbenzenes, and very preferably has pore size of from above about 5 Angstrom to about 7 Angstrom. The dehydrogenated hydrocarbon stream 25 passes to an alkylation step ALK from which passes a modified alkylbenzene product 26. An optional recycle stream is identified as 28.

Figure 3:
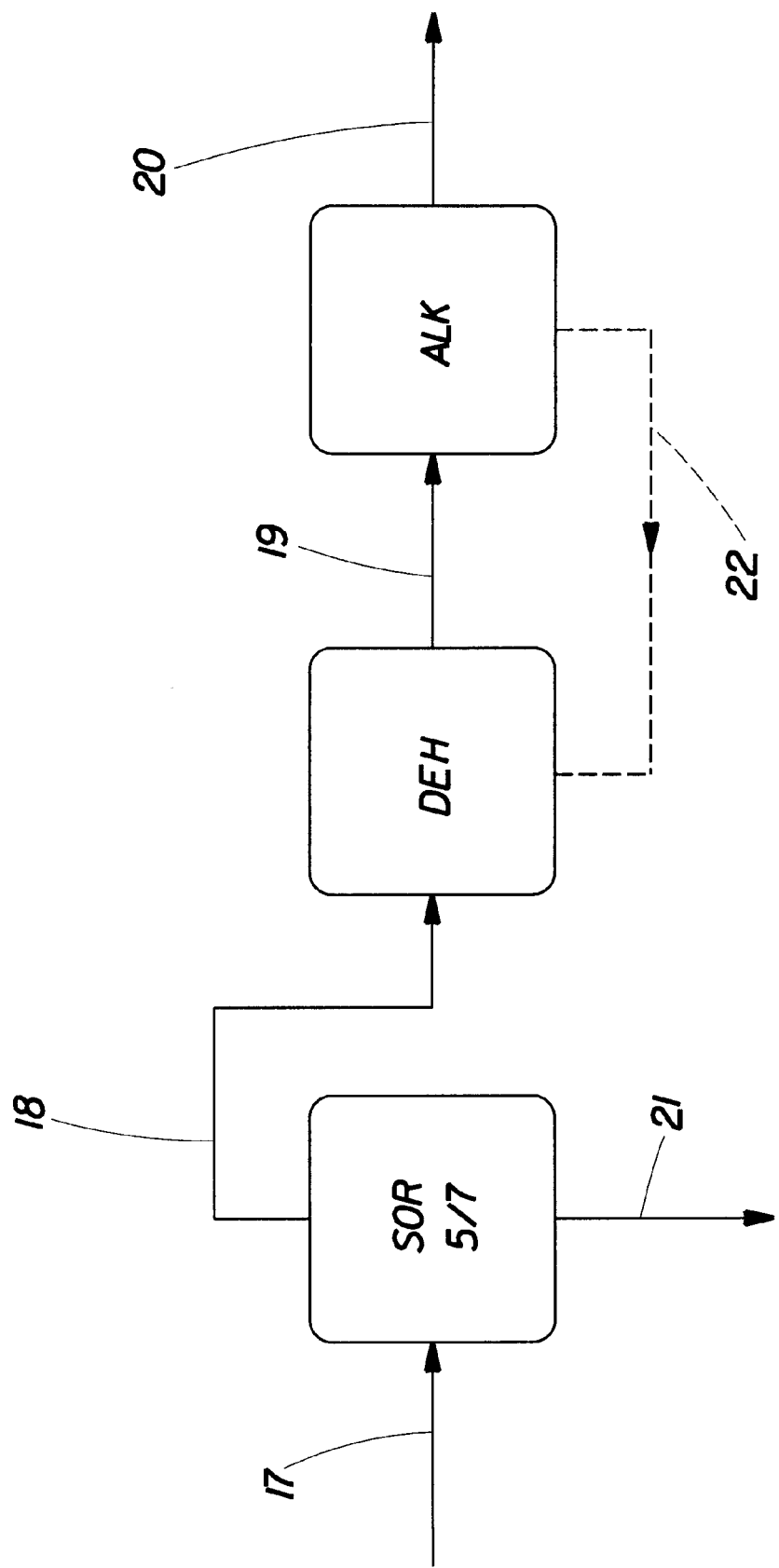

FIG. 3 is a schematic drawing identifying an embodiment of the invention similar to that of FIG. 4 but using substantially different feedstock and intermediate process stream compositions. For example, FIG. 3 can utilize as feed 17 a C10–C14 paraffin fraction having the intrinsic linear/branched paraffin ratio as received, and from which cyclics, aromatics, gem-dimethyl, ethyl- or higher-than-ethyl branched hydrocarbons are removed as part of the present process.

When comparing FIG. 3 and FIG. 4 it may appear in view of the apparently identical configuration of steps that the processes illustrated therein are identical. This is not the case in view of the very different results achieved in consequence of changing the hydrocarbon feed. FIG. 4 uses as hydrocarbon feed 23 an effluent stream from a linear alkylbenzene manufacturing facility and produces a modified alkylbenzene 26 which is predominantly branched. The FIG. 4 process could be built as an "add-on" to a standard linear alkylbenzene manufacturing plant. In contrast, FIG. 3 uses as hydrocarbon feed a mixture of linear and branched paraffins of the kind intrinsically present in, say, a jet/diesel cut derived from kerosene which has not been processed in a linear alkylbenzene manufacturing facility. The FIG. 3 process produces a modified alkylbenzene which contains a mixture of methyl-branched (unconventional, in accordance with the invention) and linear (conventional) alkylbenzenes. The FIG. 3 process can be built as a "stand-alone" facility requiring no connection to a conventional linear alkylbenzene manufacturing facility. These observations are intended to better illustrate the present process and should not be taken as limiting.

Figure 5:
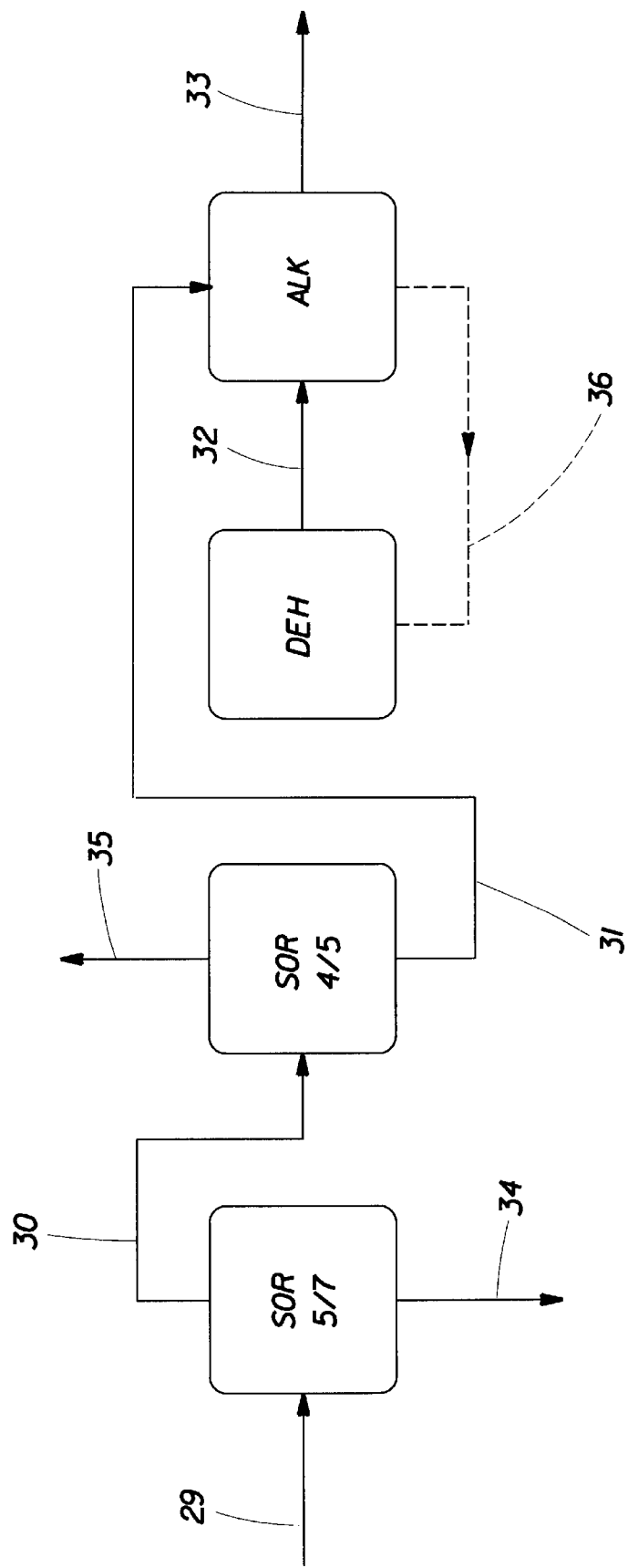
Figure 6:
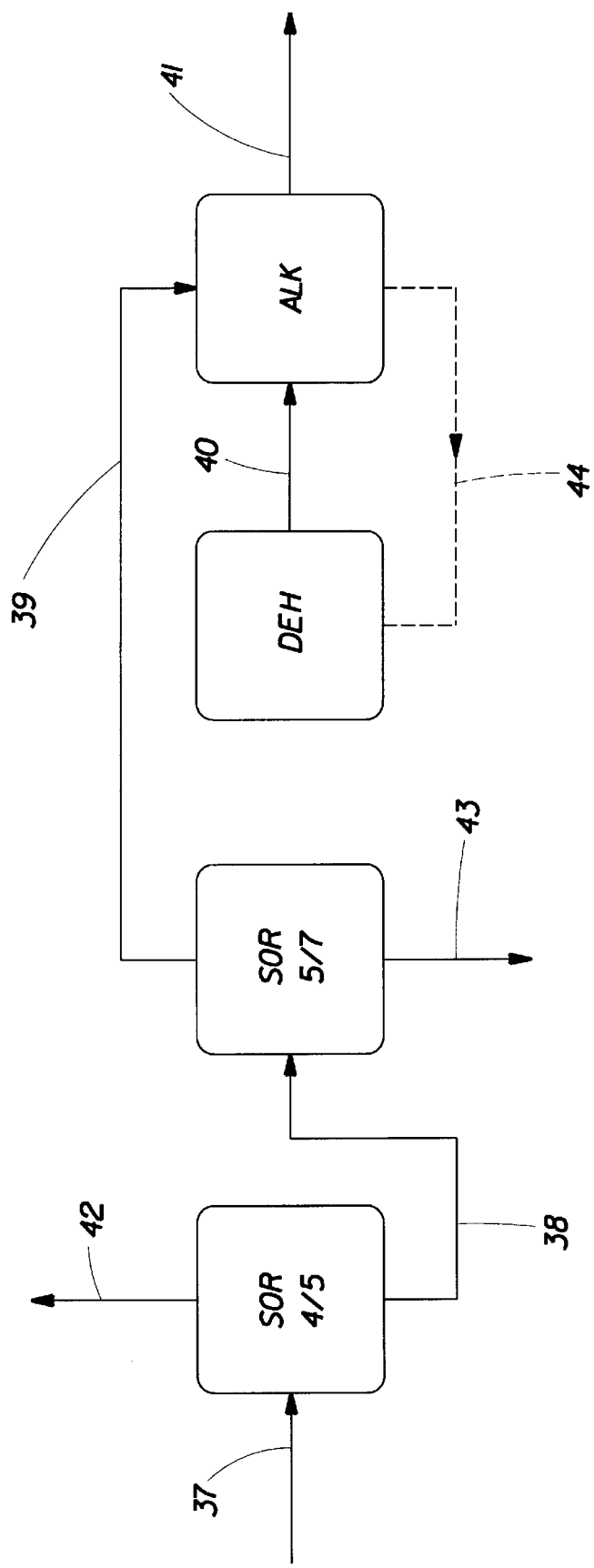
Figure 7:
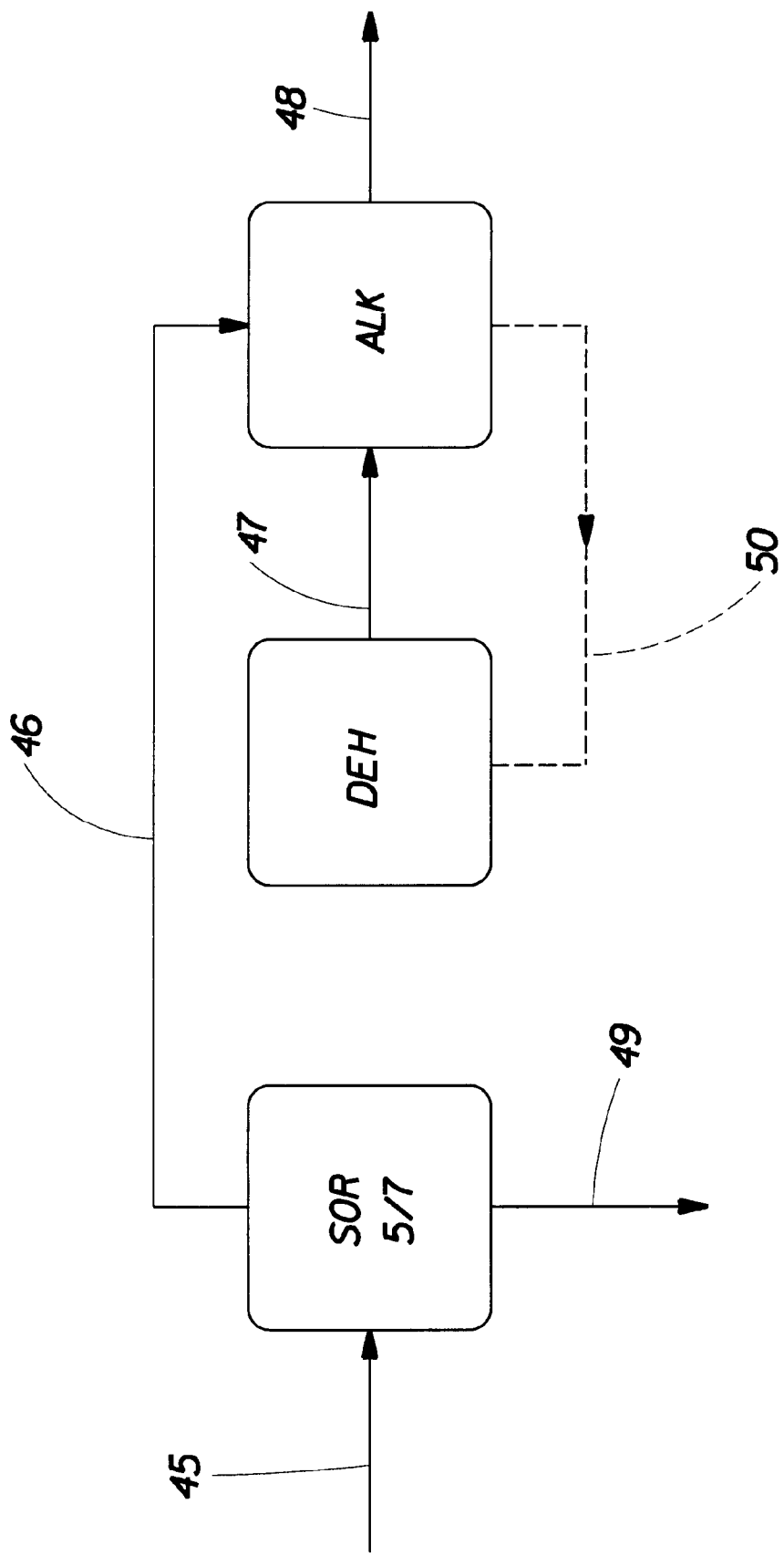

FIG. 5, FIG. 6 and FIG. 7 are schematic drawings identifying additional embodiments of the invention to accommodate other different hydrocarbon feeds. More specifically, these Figures illustrate processes which accommodate mixed paraffin/olefin feeds.

Figure 8:
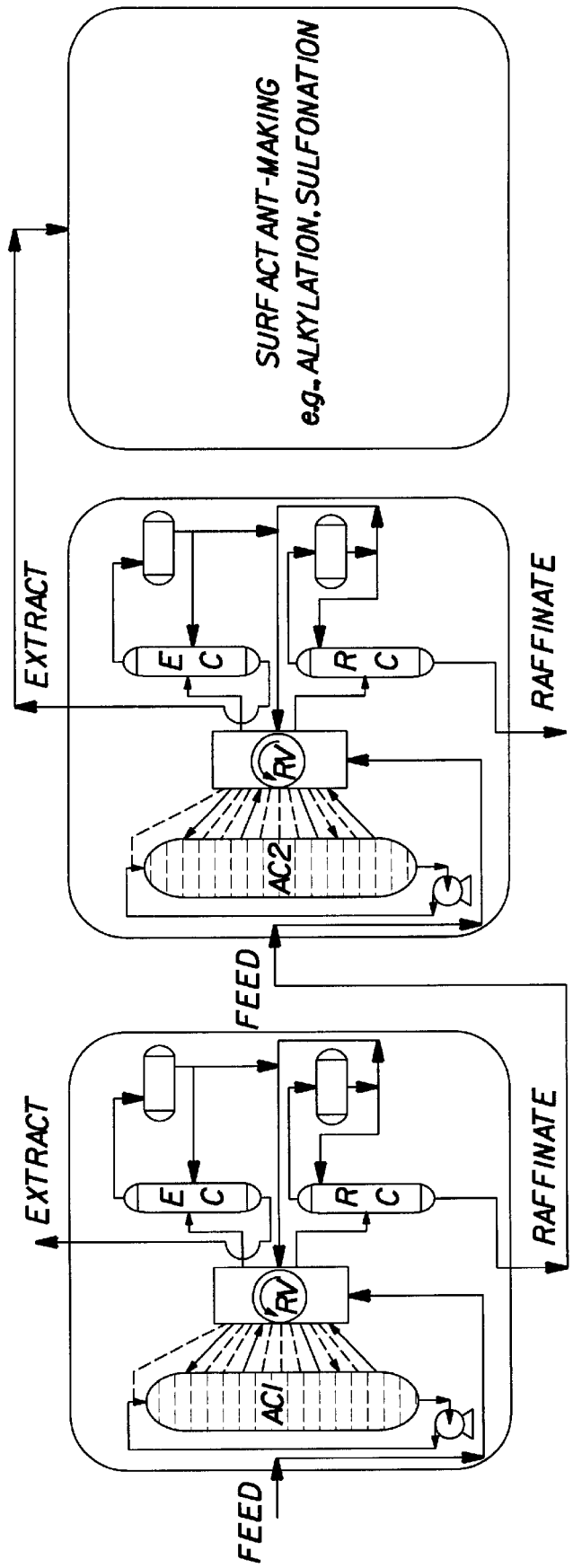
FIG. 8 shows in more detail a configuration of two adsorptive separation units, each individually being of a type as found in the first two adsorptive separation steps of FIG. 1 and FIG. 2. Note that the FIG. 8 interconnections are as shown in FIG. 1., but differ from those shown in FIG. 2.

FIG. 8 shows in more detail the particular configuration of adsorptive separations which is found in other process illustrations, e.g., in FIG. 1 and FIG. 6. Each block represents an adsorptive separation unit. Within each block, a vertical array of adsorptive separation beds (AC in the left of each block) is controlled by a rotary valve (RV). The adsorptive separation is accompanied by distillations in columns RC and EC. The streams marked "Feed", "Extract" and "Raffinate" of the leftmost adsorptive separation correspond with the streams marked "1", "6" and "2" in FIG. 1. The raffinate stream of the first adsorptive separation (and not the extract as would be the case in conventional linear alkylbenzene manufacture) becomes the feed for the second adsorptive separation. The raffinate of the second adsorptive separation in FIG. 8 corresponds with stream 7 in FIG. 1. The extract of the second adsorptive separation in FIG. 8 corresponds with stream 3 in FIG. 1: this is the stream which in the present process is dehydrogenated and/or alkylated.

FIG. 8, as noted, also serves to illustrate in more detail individual adsorptive separations herein. Thus, while the connections are not as shown in FIGS. 2,3,4,5 and 7, any single adsorptive separation of FIGS. 2,3,4,5 and 7 can be represented in more detail using an appropriate interconnection of the detailed units illustrated in either block of FIG. 8.

Finally, the convention is used in FIGS. 1–7 to depict hydrocarbon fractions adsorbed by the porous media as exiting above the adsorptive separations marked "SOR" while fractions not adsorbed are shown as exiting below the adsorptive separations marked "SOR". The fraction exiting "above" is sometimes in the art referred to as an "adsorbate" or "extract" and the fraction exiting "below" is sometimes referred to as a "raffinate" or "effluent". The "above" and "below" conventions used here are intended to make reading the process Figures more convenient and should not be taken as limiting the practical executions of the present process to any particular geometrical arrangement.

SUMMARY OF THE INVENTION

In a preferred embodiment, this invention relates to a process for preparing a modified alkylbenzenesulfonate surfactant from a hydrocarbon feed. "Modified" and other terms with special usage are defined in the detailed description hereinafter. "Modified" connotes a very particular type of branching. The processes comprise (a) a particularly defined adsorptive separation stage and, when making modified alkylbenzenes and/or alkylbenzenesulfonates, (c) an alkylation stage. Of significant utility for the manufacturer of detergents, the hydrocarbon feed can be an adsorptive separation raffinate or effluent deriving from a linear alkylbenzene manufacturing process, though other feeds, such as jet/diesel or olefins can be used.

When the feed is paraffinic, process embodiments typically and preferably further include (b) a dehydrogenation stage inserted in the sequence between the adsorptive separation and the alkylation and (c) an alkylation stage. When the feed is olefin, quite evidently, dehydrogenation is not essential. In general, the alkylation stage is preferably followed by (d) sulfonation; (e) neutralization; and (f) formulation into consumer cleaning products by mixing, agglomeration, compaction, spray-drying and the like. Any stage can have more than one step and include options such as distillation, provided that it includes at least the specified minimum.

Stage (a), adsorptive separation, comprises at least partially separating the hydrocarbon feed selected from olefinic feeds, paraffinic feeds and mixed olefinic/paraffinic feeds, into at least one branched-enriched stream comprising an increased proportion (e.g., in relative terms at least about 50% higher, and in absolute terms, that is in terms of percentage by weight, at least about 10% by weight) of branched acyclic hydrocarbons relative to said hydrocarbon feed and typically, one or more additional streams, for example at least one linear-enriched stream comprising an increased proportion (e.g., in relative terms at least about 50% higher, and in absolute terms at least about 10% by weight) of linear acyclic aliphatic hydrocarbons relative to said hydrocarbon feed. Other streams present in the process can vary in composition. Such streams include reject streams, in which cyclic and/or aromatic undesirable components from the feeds are present at levels generally exceeding those of the feed; recycle streams and the like can also be present.

In more detail, the adsorptive separation part, (a), of the process has one or more steps comprising first, providing the hydrocarbon feed, then at least one step selected from adsorptive separation using porous media (preferred), clathration using a clathrating compound selected from urea, thiourea and alternative clathrating amides; and combinations thereof. This stage uses simulated moving bed adsorptive separation means known from the art (see in particular U.S. Pat. No. 2,985,589 incorporated herein in its entirety) comprising both of at least one bed holding said porous media or clathrating compound (see, for example U.S. Pat. No. 2,985,589 FIG. 1 and the associated description) and a device, typically a rotary valve of a highly specialized design, for simulating motion of said porous media or clathrating compound countercurrent to a hydrocarbon stream in said bed. (see in particular U.S. Pat. No. 2,985,589 FIG. 2).

Particularly unusual and novel in the context of the present process is that, at minimum, the simulated moving-bed adsorptive separation herein is used to extract an essential branched-enriched stream, that is, the exact opposite of the practice used in linear alkylbenzenesulfonate surfactant manufacture. This essential difference is also associated with having a different contents of the bed as compared to conventional practice, that is, there is at least one bed containing porous media differing from the 4–5 Angstrom zeolites normally used for linear alkylbenzene manufacture by having larger pore size and reconfiguring the process equipment, notably said bed and said device, so that they connect differently with the associated process steps. More specifically, these means are configured such that the branched stream is passed on through the process, while any linear-enriched streams, however useful for other purposes, are either rejected from the present process or are present in accompaniment of branched-enriched streams. Moreover, stage (a) of the instant process suitably comprises use of at least one porous medium selected from the group consisting of porous media having a minimum pore size at least larger than the pore size required for selective adsorption of linear acyclic hydrocarbons, said pore size not exceeding about 20 Angstroms, more preferably not exceeding about 10 Angstroms.

When said hydrocarbon feed comprises more than about 10% of paraffins, and invariably with higher levels, e.g., about 11% to 90% or higher of paraffins, the present process preferably includes an additional step, (b), of at least partially dehydrogenating said branched-enriched stream. Dehydrogenation can be done using known catalysts and conditions.

Regardless of the type of feed, the present process preferably comprises (c) reacting a branched-enriched stream prepared by one or both of the preceding steps (adsorptive separation optionally with dehydrogenation provided that the branched-enriched stream ultimately comprises olefin, typically at least about 5%, more typically at least about 15% of olefins, generally 5% to 90% or higher) with an aromatic hydrocarbon selected from benzene, toluene and mixtures thereof in the presence of an alkylation catalyst. The preferred alkylation step herein has a low internal isomer selectivity of from 0 to no more than about 40, preferably no more than about 20, and is described and defined more fully elsewhere herein. Such low alkylation selectivity alkylations are believed novel in their own right in the context of modified alkylbenzene manufacture.

Preferred processes herein further preferably meet at one least one, and more preferably both, of the following requirements: As the first requirement, said stage (a) means comprise one, two or more of said devices and at least two of said beds, at least one of said beds comprising porous media differentiated relative to the contents of another of said beds by an increased capacity to retain methyl-branched acyclic aliphatic hydrocarbons. For example, zeolites having pore size of above about 5 to no more than about 7 Angstrom are especially preferred. As the second requirement, said step (c) has an internal isomer selectivity of from 0 to no more than about 40, preferably lower as further defined hereinafter.

Preferred processes herein operate in a manner contradictory to and inconsistent with conventional practice for making alkylbenzenesulfonate surfactants, which accept linear materials for further processing and reject most branched materials. Further, in order to achieve this reversal, it is found necessary to make use of an unconventional interconnection of adsorptive separation operations as further described and illustrated in the Figures of this specification.

Also in preferred processes herein, said simulated moving bed adsorptive separation means in said stage (a) comprise not one, but two of said devices. The number of devices taken in conjunction with their configuration is of especial importance in accomplishing the manufacture of the preferred compositions of the invention and increases specific types of branching in the hydrocarbon streams.

Further, in certain preferred processes having two of said beds, each comprises a different member of said porous media, each of said beds being controlled by one of said devices, and each of said devices having a minimum of eight ports (as defined in U.S. Pat. No. 2,985,589) for achieving simulated movement of said porous media in said beds. Each of said beds is further preferably divided into a vertically positioned array of at least eight sub-beds. (See FIG. 1 in U.S. Pat. No. 2,985,589). Also preferably, stage (a) uses exclusively porous media, rather than clathrating compounds, in said beds.

Processes herein can have one or more steps following the alkylation step. Such steps can include the additional step of (d) sulfonating the product of step (c). Sulfonation can be followed by the additional step of (e) neutralizing the product of step (d). Such steps can be followed by (f) mixing the product of step (d) or (e) with one or more cleaning product adjunct materials; thereby forming a cleaning product.

The present invention also encompasses modified alkylbenzene produced by any of the processes herein; as well as modified alkylbenzenesulfonic acid or modified alkylbenzenesulfonate surfactant in any known salt form such as the sodium form, the potassium form, the ammonium form, the substituted ammonium form or the like, produced by any of the processes herein; as well as consumer cleaning product produced by any of the processes herein.

Cleaning product embodiments herein include laundry detergents, dishwashing detergents, hard surface cleaners and the like. In such embodiments, the content of modified alkylbenzenesulfonate produced by the instant process is from about 0.0001% to about 99.9%, typically from about 1% to about 50%, and the composition further comprises from about 0.1% to about 99.9%, typically from about 1% to about 50%, of cleaning product adjunct materials such as cosurfactants, builders, enzymes, bleaches, bleach promoters, activators or catalysts, and the like.

The present invention also has alternate embodiments using paraffinic hydrocarbon feeds, in which two adsorptive separations, particularly configured in much the same manner as stage (a) described herein for modified alkylbenzene production, are followed by additional steps other than benzene alkylation step (c), and leading to useful cleaning surfactants. Such steps replacing the step (c) alkylation can include at least one step selected from: dehydrogenation, chlorination, sulfoxidation, oxidation to a C8–C20 alcohol and oxidation to a C8–C20 carboxylic acid or salt thereof, optionally followed by one of: glucosamidation, conversion to a nonsaccharide-derived amide surfactant (for example a monoethanolamide surfactant or any such amide not having a glucose moiety), and sulfonation as ester. Other alternative embodiments use a hydrocarbon feed comprising 20% or more of methyl-branched olefins; again, this process has the particularly configured stage (a) adsorptive separations. Subsequent steps can include alkylation with benzene or toluene optionally followed by sulfonation; alkylation with phenol followed by at least one of alkoxylation, sulfation, sulfonation or combinations thereof, hydroformylation to alcohol optionally followed at least one of alkoxylation, glycosylation, sulfation, phosphation or combinations thereof, sulfonation; epoxidation; hydrobromination followed by amination and oxidation to amine oxide; and phosphonation.

The invention also encompasses the surfactants produced by such processes and the cleaning products produced by such processes. The present invention moreover includes especially useful embodiments wherein the adsorptive separations of stage (a) comprise at least one separation step using an organometallic-grafted mordenite such as a tin-grafted mordenite. The invention also encompasses a method comprising use of a grafted mordenite for manufacturing detergent surfactants and any of the corresponding surfactants and consumer products produced by use of these specific porous media in any of the above-defined processes.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

In one embodiment, the present invention relates to a process for preparing a modified alkylbenzenesulfonate surfactant from a hydrocarbon feedstock. The equivalent terms "feed" and/or "feedstock" are used herein to identify any hydrocarbon useful as a starting material in the present process. In contrast, the term "stream" is typically used to identify hydrocarbon which has undergone at least one process step. The hydrocarbon feed herein in general contains useful proportions of acyclic aliphatic hydrocarbons, whether olefinic or paraffinic, or may include mixtures of such olefins and paraffins. The raw feedstock further typically includes varying amounts of cyclic and/or aromatic impurities, as found for example in jet/diesel hydrocarbon cuts. In the feedstock, the olefins and paraffins generally occur in both branched and linear forms. Moreover, in general, the branched forms in the feedstock can be either undesirable or desirable for the present purposes. The present purposes of providing cleaning products differ markedly, for example, from gasoline manufacture in which a high degree of polymethyl branched hydrocarbons is desirable for increasing octane rating. The present invention provides processes for separating particular desired forms of the hydrocarbon feeds for cleaning product purposes, and of incorporating them into surfactants (especially certain modified alkylbenzene sulfonates) and into cleaning products and useful surfactant intermediates for such products.

The term "modified" as applied in connection with any product of the present process means that the product contains a very particular type of branching and surprisingly departs from the linear structure which is now commonly taught to be preferred and used for cleaning product surfactants. The term "modified" is further used to differentiate the products herein from conventional highly-branched cleaning surfactant structures, such as those found in tetrapropylene benzene sulfonates, and from all other conventional branched structures such as "two-tailed" or "Guerbet" or aldol-derived branched structures.

Hydrocarbon feeds herein can in general vary quite widely but typically include methyl-branches such as monomethyl, dimethyl (including gem-dimethyl), trimethyl, polymethyl, ethyl, and higher alkyl branches. The hydrocarbon feeds may contain quaternary carbon atoms. The desirable components for the present purposes include monomethyl-branched, dimethyl-branched other than gem-dimethyl-branched, and to some extent, especially at carbon contents in excess of about 14, some proportion of trimethyl-branched. The hydrocarbon feeds include useful proportions, e.g., 5%–40% or more, of acyclic hydrocarbons having in general from about 9 to about 20 carbon atoms depending on the desired type of cleaning product surfactant or the cleaning product use of the modified surfactant being produced. More preferably, when making alkylbenzenes and alkylbenzenesulfonates herein, the acyclic aliphatic hydrocarbons of the feedstock comprise from about 10 to about 16, more preferably from about 11 to about 14 carbon atoms.

The present processes comprise a particularly defined adsorptive separation stage and, for the purposes of making modified alkylbenzenes and alkylbenzenesulfonates, an alkylation stage is also essential. When the feedstock is paraffinic, process embodiments typically and preferably further include a dehydrogenation stage inserted in the sequence between the adsorptive separation and the alkylation. In general, the alkylation stage can be followed by additional steps such as sulfonation, typically followed by neutralization and formulation into consumer cleaning products by mixing, agglomeration, compaction, spray-drying and the like. Also in general, any stage can have more than one step provided that it includes at least the minimum of one step.

Stage (a), adsorptive separation, comprises at least partially separating the hydrocarbon feed selected from olefinic feeds, paraffinic feeds and mixed olefinic/paraffinic feeds into at least one branched-enriched stream comprising an increased proportion (e.g., in relative terms compared to the feed at least about 50% higher, more preferably at least about 100% higher, typically treble, quadruple or more and in absolute terms, that is in terms of percentage by weight, at least about 10% by weight, typically at least 20%, more preferably from 30% to about 90% or more) of branched acyclic hydrocarbons (especially the desired types identified supra, particularly methyl-branched paraffins or methyl-branched mono-olefins) relative to said hydrocarbon feed and optionally, one or more of: a linear-enriched stream comprising an increased proportion (e.g., in relative terms at least about 50% higher, more preferably at least about 100% higher, typically treble, quadruple or more and in absolute terms at least about 10% by weight, typically at least 20%, more preferably from 30% to about 90% or more) of linear acyclic aliphatic hydrocarbons relative to said hydrocarbon feed; and a reject stream comprising cyclic and/or aromatic hydrocarbons or other impurities such as gem-dimethyl hydrocarbons, ethyl-branched hydrocarbons or higher-branched hydrocarbons.

Other streams present anywhere in the present process can vary in composition. Such streams include reject streams, in which cyclic and/or aromatic undesirable components from the feeds are present at levels generally exceeding those of the feed; recycle streams having compositions depending on the parts of the process they connect, and the like. Known processes, such as that of U.S. Pat. No. 5,012,021 or U.S. Pat. No. 4,520,214 both incorporated by reference, can be used herein to convert impurities, such as certain diolefins, back to monoolefins using a selective catalyst. Other processes which can optionally be incorporated herein to selectively remove aromatic byproducts formed in paraffin dehydrogenation include those of U.S. Pat. No. 5,300,715 and U.S. Pat. No. 5,276,231 involving the use of one or more aromatic removal zones and/or extractants for aromatics which may include, for example, sulfolane and/or ethylenediamine.

In more detail, the adsorptive separation stage or part of the process has one or more steps comprising at least one step selected from providing a suitable hydrocarbon feed and at least one step selected from adsorptive separation using porous media, clathration using a clathrating compound selected from urea, thiourea and alternative clathrating amides; and combinations thereof Very preferably, when using combinations, at least one step is an adsorptive separation using porous media of the larger-pore type described more fully hereinafter. Stage (a) uses simulated moving bed adsorptive separation means well known from the art (see in particular U.S. Pat. No. 2,985,589 incorporated herein in its entirety) comprising both of at least one bed holding said porous media or clathrating compound (see, for example U.S. Pat. No. 2,985,589 FIG. 1 and the associated description) and a device for simulating motion of said porous media or clathrating compound countercurrent to a hydrocarbon stream in said bed. (see in particular U.S. Pat. No. 2,985,589 FIG. 2 and the associated description, or variants in current commercial use for the production of linear alkylbenzenesulfonates). The device in question is typically a rotary valve of a highly specialized design. In general, types of such valves as used in current linear alkylbenzene can be used herein. Adsorptive separation conditions, e.g., pressures, temperatures and times, can be as used in the art. See, for example, U.S. Pat. No. 2,985,589.

What is particularly unusual and novel in the context of the present process is that, at minimum, the simulated moving-bed adsorptive separation herein is used to extract an essential branched-enriched stream, that is, the exact opposite of the practice used in linear alkylbenzenesulfonate surfactant manufacture. This essential difference is also associated with changing the contents of the bed so that it contains porous media differing from the 4–5 Angstrom zeolites normally used for linear alkylbenzene manufacture, and reconfiguring the process equipment, notably said bed and said device, so that they connect differently with the associated process steps. More specifically, these means are configured such that the branched stream is passed on through the process, while any linear-enriched streams, however useful for other purposes, are either rejected from the present process or are present in accompaniment of branched-enriched streams.

When said hydrocarbon feed comprises less than about 5% of olefins, the present process preferably includes an additional step, (b), of at least partially dehydrogenating the product of stage (a). Dehydrogenation can be done using any known dehydrogenation catalyst, such as the De-H series from UOP, and are further illustrated hereinafter. Dehydrogenation conditions are similar to those used in current linear alkylbenzenesulfonate manufacture.

Regardless of the type of feedstock treated, the present process preferably comprises (c) reacting the product of stage (a), or when step (b) is also present in the foregoing steps, the product of stage (a) followed by (b), with an aromatic hydrocarbon selected from benzene, toluene and mixtures thereof in the presence of an alkylation catalyst. The preferred alkylation step herein has a low internal isomer selectivity of from 0 to about 40, preferably not more than about 20, more preferably not more than about 10, as described and defined more fully elsewhere herein. Such low internal isomer selectivities are believed novel in their own right.

In one mode, the alkylation step herein is run in the presence of excess paraffin, which is then recovered and recycled to the dehydrogenator. In another mode, the alkylation step is run in presence of 5x to 10x excess of arene. Any combination of such modes is possible.

Note that when the final branched-enriched stream, i.e., the product of stage (a), has appreciable olefin content, e.g., more than about 5% olefins in total, this stream can proceed directly to the alkylation step (c), then recovered paraffins can be recycled to a dehydrogenation reactor for at least partial conversion to olefin. See, for example, FIGS. 5, 6, 7.

Of great importance to the present invention, preferred processes herein further preferably meet at one least one, and more preferably both, of the following requirements: As the first requirement, said stage (a) means comprise one, two or more of said devices (e.g., the aforementioned rotary valves or any equivalent means) and at least two of said beds, at least one of said beds comprising porous media differentiated relative to the contents of another of said beds by an increased capacity to retain methyl-branched acyclic aliphatic hydrocarbons. For example, zeolites having pore size at least in excess of sizes used in conventional linear alkylbenzene manufacture and up to about 20 Angstrom, more preferably up to about 10 Angstrom, more preferably still up to about 7 Angstrom, or other porous media such as certain silicoaluminophosphates or Mobil MCM-type materials are suitable herein provided that the pore sizes are as noted. When using porous materials having pore sizes above about 7 Angstrom, it is often highly desirable to "tune down" the pore openings, for example by grafting of tin alkyls at the pore openings. See EP 559,510 A incorporated herein by reference in its entirety. As the second requirement, said step (c) has an internal isomer selectivity of from 0 to no more than about 40, preferably lower, as noted supra and as further defined in detail hereinafter.

In other preferred processes, at least one of said beds comprises porous media conventional for the manufacture of linear alkylbenzenes; said beds being connected into said process in a manner consistent with at least partially increasing the proportion of methyl-branched acyclic aliphatic hydrocarbons in streams passing to step (c) of said process, and at least partially decreasing the proportion of linear acyclic aliphatic hydrocarbons passing to step (c) of said process, said linear acyclic aliphatic hydrocarbons being at least partially removed as effluent in stage (a). In other words, preferred processes herein operate in a manner contradictory to and inconsistent with conventional practice for making alkylbenzenesulfonate surfactants, which reject branched materials and accept linear materials for further processing. Further, in order to achieve this reversal, it is found necessary to make use of an unconventional interconnection of adsorptive separation operations as already briefly described and as further illustrated in the Figures herein.

Also of great importance, in preferred processes herein, said simulated moving bed adsorptive separation means in said stage (a) comprise not one, but two of said devices, or a single device capable of simulating movement of said porous media in at least two independent beds. In other words, for all preferred processes herein, using a single device, for example a device as taught in U.S. Pat. No. 2,985,589, will not suffice. The number of devices taken in conjunction with their configuration is of especial importance in accomplishing the manufacture of the preferred compositions of the invention. Thus, in a hypothetical not known from the art, an increasing purification of a linear hydrocarbon might be accomplished by two devices and two beds connected in series. A highly linear adsorbate of the first stage might proceed to a second stage adsorptive separation process inlet for further purification. Such a configuration is outside the present invention on account of its incorrect connection of the stages, which lead to increasing the linearity and purity of a hydrocarbon. The present processes, as has already been noted, involve passing branched streams though the various steps or stages, requiring a connection of the devices which is consistent with the objective. This increases specific types of branching in the hydrocarbon streams herein.

Further of great importance in preferred processes herein, there are two of said beds, each comprising a different member of said porous media, each of said beds being controlled by one of said devices, and each of said devices having a minimum of eight ports for achieving simulated movement of said porous media in said beds. Each of said beds is further preferably divided into a vertically positioned array of at least eight sub-beds. Also preferably, stage (a) uses exclusively porous media in said beds. Thus, the invention can make use of conventional beds and devices of the general type described in U.S. Pat. No. 2,985,589; but their number and connection into the present process is novel and unprecedented in alkylbenzenesulfonate manufacturing plants.

Also, the better to illustrate what has already been described, in certain embodiments of preferred processes herein, said linear-enriched stream is present in stage (a) and stage (a) comprises: (a-i) adsorptive separation of said hydrocarbon feed into said linear-enriched stream and an intermediate branched-enriched stream and rejection of said linear-enriched stream for essential purposes of said process, by means of one of said simulated moving beds; followed by (a-ii) adsorptive separation of said intermediate branched-enriched stream into said branched-enriched stream comprising an increased proportion of branched (more particularly methyl-branched) acyclic aliphatic hydrocarbons relative to said linear-enriched stream, and a reject stream comprising at least an increased proportion of cyclic and/or aromatic hydrocarbons relative to said branched-enriched stream, by means of another of said simulated moving beds.

Said reject stream in said step (a-ii) can further comprise undesired branched hydrocarbons selected from gem-dimethyl branched hydrocarbons, ethyl branched hydrocarbons and higher than ethyl branched hydrocarbons; and wherein the acyclic aliphatic hydrocarbons of said intermediate branched-enriched stream and said branched-enriched stream comprise a reduced proportion of said gem-dimethyl branched hydrocarbons, ethyl branched hydrocarbons and higher than ethyl branched hydrocarbons relative to said hydrocarbon feed. In general, a minimum of "increasing proportion", "decreasing proportion", or "enriching" of any component in any step herein corresponds to any increase (enrichment) or decrease in proportion useful for the practically stated purposes of the invention. Such amounts are well illustrated throughout the specification.

Also in said process, said stream compositions can be achieved by selecting as said porous media: a member selected from the group consisting of 4–5 Angstrom pore-size zeolites in said step (a-i) and a member selected from the group consisting of porous media having a pore size at least greater than about the maximum pore size of said step (a-i) zeolite and at most about 10 Angstrom in said step (a-ii).

In another preferred embodiment, stage (a) comprises: (a-i) adsorptive separation of said hydrocarbon feed into an acyclic aliphatic hydrocarbon-enriched stream comprising linear- and branched (such as the desirable types described supra) acyclic aliphatic hydrocarbons and a first reject stream comprising at least an increased proportion of cyclic and/or aromatic hydrocarbons relative to said hydrocarbon feed, followed by (a-ii) adsorptive separation of said acyclic aliphatic hydrocarbon-enriched stream into said branched-enriched stream and said linear-enriched stream; wherein said adsorptive separations are accomplished using said simulated moving bed adsorptive separation means. Unless otherwise noted herein, the "branched-enriched stream" is the final stream of stage or step (a); additional qualifiers such as "intermediate" will otherwise be prefixed on the name to indicate that the stream, though enriched in branched hydrocarbons, requires further treatment before proceeding from the adsorptive separation stages of the instant process to other stages. Also to be noted, stage (a), the adsorptive separation stage, can freely include other conventional, optional steps, such as distillation, provided that adsorptive separation is conducted. Thus, current commercial MOLEX® plants will typically further include distillation in this stage and can be useful herein.

The invention further encompasses a process wherein said first reject stream in said step (a-i) further comprises undesired branched hydrocarbons selected from gem-dimethyl branched hydrocarbons, ethyl branched hydrocarbons and higher than ethyl branched hydrocarbons; and wherein said acyclic aliphatic hydrocarbon-enriched stream and said branched-enriched stream each comprises a reduced proportion of said gem-dimethyl branched hydrocarbons, ethyl branched hydrocarbons and higher than ethyl branched hydrocarbons relative to said hydrocarbon feed. In such embodiments, stream compositions can be achieved by selecting as said porous media: a member selected from the group consisting of 4–5 Angstrom pore-size zeolites in said step (a-ii) and a member selected from the group consisting of porous media having a pore size at least greater than about the maximum pore size of said step (a-ii) zeolite and at most about 10 Angstrom in said step (a-i).

More generally, the invention relates to a process wherein stage (a) comprises use of at least one porous medium selected from the group consisting of porous media having a minimum pore size larger than the pore size required for selective adsorption of linear acyclic hydrocarbons, said pore size not exceeding about 20 Angstroms.

As noted, preferred processes herein include those wherein said alkylation step, (c), has an internal isomer selectivity of from 0 to 20; also, a preferred alkylation step, (c) uses an alkylation catalyst consistent with said internal isomer selectivity, and wherein said alkylation catalyst is selected from the group consisting of: at least partially acidic mordenites and at least partially acidic zeolite beta. Preferred alkylation catalysts include H-mordenites and H-beta, more preferably H-mordenite, which is at least partially dealuminized.

The invention also preferably includes the process wherein said hydrocarbon feed comprises at least about 10% methyl-branched paraffins having molecular weight of at least about 128 and no more than about 282; said process having said dehydrogenation step (b). More preferably in such embodiments, said hydrocarbon feed comprises at least about 20% methyl-branched paraffins having molecular weight of at least about 128 and no more than about 226; said process having said dehydrogenation step (b) and having alkylation step (c).

The invention also preferably includes the process wherein said hydrocarbon feed comprises at least about 10% methyl-branched olefins having molecular weight of at least about 126 and no more than about 280. More preferably in such embodiments, the hydrocarbon feed comprises at least about 50% methyl-branched olefins having molecular weight of at least about 126 and no more than about 224; said process having no dehydrogenation step (b).

Of significant utility for the manufacturer of detergents, the hydrocarbon feed or feedstock herein can be an adsorptive separation raffinate or effluent deriving from a linear alkylbenzene manufacturing process.

Processes herein can have one or more steps following the alkylation step. Such steps can include the additional step of (d) sulfonating the product of step (c). Sulfonation can be followed by the additional step of (e) neutralizing the product of step (d). Such steps can be followed by (f) mixing the product of step (d) or (e) with one or more cleaning product adjunct materials; thereby forming a cleaning product.

Thus the process herein includes highly preferred embodiments having all of the additional steps of (d) sulfonating the modified alkylbenzene product of step (c); (e) neutralizing the modified alkylbenzenesulfonic acid product of step (d); and (f) mixing the modified alkylbenzenesulfonic acid or modified alkylbenzenesulfonate surfactant product of steps (d) or (e) with one or more cleaning product adjunct materials; thereby forming a cleaning product. In one such embodiment, prior to said sulfonation step, modified alkylbenzene which is the product of said step (c) is blended with a linear alkylbenzene produced by a conventional process. In another such embodiment, in any step subsequent to said sulfonation step, modified alkylbenzene sulfonate which is the product of said step (d) is blended with a linear alkylbenzene sulfonate produced by a conventional process. In these blended embodiments, a preferred process has a ratio of modified alkylbenzene to linear alkylbenzene of from about 1:100 to about 100:1. When a relatively more linear product is desired, a preferred ratio is from about 10:90 to about 50:50. When a relatively more branched product is desired, a preferred ratio is from about 90:10 to about 51:49.

The present invention also encompasses modified alkylbenzene produced by any of the processes herein; as well as modified alkylbenzenesulfonic acid or modified alkylbenzenesulfonate surfactant in any known salt form such as the sodium form, the potassium form, the ammonium form, the substituted ammonium form or the like, produced by any of the processes herein; as well as consumer cleaning product produced by any of the processes herein.

Cleaning product embodiments herein include laundry detergents, dishwashing detergents, hard surface cleaners and the like. In such embodiments, the content of modified alkylbenzenesulfonate produced by the instant process is from about 0.0001% to about 99.9%, typically from about 1% to about 50%, and the composition further comprises from about 0.1% to about 99.9%, typically from about 1% to about 50%, of cleaning product adjunct materials such as cosurfactants, builders, enzymes, bleaches, bleach promoters, activators or catalysts, and the like.

Preferred consumer cleaning products produced by these processes suitably comprise from about 1% to about 50% of said modified alkylbenzenesulfonic acid and from about 0.0001% to about 99% of cleaning product adjunct materials selected from enzymes, nonphosphate builders, polymers, activated bleaches, catalyzed bleaches, photobleaches and mixtures thereof Alternate Process Embodiments The present invention has alternate embodiments in which two particularly configured adsorptive separations are followed by additional steps which lead to useful cleaning surfactants. Thus, there is encompassed herein a process comprising: (I) separating a hydrocarbon feedstock into a branched hydrocarbon-enriched stream comprising, more preferably consisting essentially of, at least about 85% of saturated acyclic aliphatic hydrocarbons having a carbon content of from about C8 to about C20, said branched hydrocarbon-enriched stream comprising at least about 10% of paraffins having methyl branches, said methyl branches being distributed in said paraffins such that any paraffin molecule has from 0 to no more than about 3 of said methyl branches and said branches being positioned within said paraffins to an extent that at least about 90% of said branches occupy positions other than those forming gem-dimethyl and/or quaternary moieties; wherein said separation is conducted by means including at least two adsorptive separation steps using simulated moving bed adsorptive separation means and at least two porous media having different pore sizes; and (II) converting said branched hydrocarbon enriched stream to a surfactant by further steps including at least one step selected from: dehydrogenation, chlorination, sulfoxidation, oxidation to a C8–C20 alcohol and oxidation to a C8–C20 carboxylic acid or salt thereof, optionally followed by one of: glucosamidation, conversion to a nonsaccharide-derived amide surfactant and sulfonation as ester.

Further by way of alternate embodiments, there is encompassed herein a process comprising: (I) separating a hydrocarbon feedstock into a olefinic branched hydrocarbon-enriched stream comprising, preferably consisting essentially of, mixtures of olefinic acyclic aliphatic hydrocarbons having a carbon content of from about C8 to about C20 or mixtures thereof with their saturated analogs, said branched hydrocarbon-enriched stream comprising at least about 10% of the sum of said olefins and their saturated analogs having methyl branches, said methyl branches being distributed in said mixtures such that any of said acyclic aliphatic hydrocarbon molecules has from 0 to no more than about 3 of said methyl branches and said branches being positioned within said acyclic aliphatic hydrocarbon molecules to an extent that at least about 90% of said branches occupy positions other than those forming gem-dimethyl moieties; wherein said separation is conducted by means including at least two adsorptive separation steps using simulated moving bed adsorptive separation means and at least two porous media having different pore sizes; and (II) converting said olefinic branched hydrocarbon enriched stream to a surfactant by further steps including at least one step selected from: alkylation with benzene or toluene optionally followed by sulfonation; alkylation with phenol followed by at least one of alkoxylation, sulfation, sulfonation or combinations thereof; hydroformylation optionally followed at least one of alkoxylation, alkoxylation combined with oxidation, glycosylation, sulfation, phosphation or combinations thereof; sulfonation; epoxidation; hydrobromination followed by amination and oxidation to amine oxide; and phosphonation.

In view of the alternate processes encompassed, the invention also encompasses the surfactants produced by such processes and the cleaning products produced by such processes.

Aspects of the invention will now be discussed and illustrated in more detail.

Modified Alkylbenzenes and Alkylbenzenesulfonate Products

As noted in summary, the present invention includes a process for preparing modified alkylbenzenesulfonate surfactants suitable for use in cleaning products such as laundry detergents, hard surface cleaners, dishwashing detergents and the like.

The terms "modified alkylbenzenesulfonate surfactant" and "modified alkylbenzene" refer products of the processes herein. The term "modified" as applied either to the novel alkylbenzenesulfonate surfactants or to the novel alkylbenzenes (MAB) is used to indicate that the product of the present process is compositionally different from that of all alkylbenzenesulfonate surfactants hitherto used in commerce in consumer cleaning compositions. Most particularly, the instant compositions differ compositionally from the so-called "ABS" or poorly biodegradable alkylbenzenesulfonates, and from the so-called "LAS" or linear alkylbenzenesulfonate surfactants. Conventional LAS surfactants are currently commercially available through several processes including those relying on HF-catalyzed or aluminum chloride-catalyzed alkylation of benzene. Other commercial LAS surfactants include LAS made by the DETAL® process. Preferred alkylbenzenesulfonate surfactants herein made using the preferred low-internal isomer selectivity alkylation step herein are also compositionally different from those made by alkylating linear olefins using fluoridated zeolite catalyst systems, believed also to include fluoridated mordenites. Without being limited by theory, it is believed that the modified alkylbenzenesulfonate surfactants herein are uniquely lightly branched. They typically contain a plurality of isomers and/or homologs. Often, this plurality of species (often tens or even scores) is accompanied by a relatively high total content of 2-phenyl isomers, 2-phenyl isomer contents of at the very least 25% and commonly 50% or even 70% or higher being attained. Moreover the modified alkylbenzenesulfonate products herein differ in physical properties from known alkylbenzenesulfonate surfactants, for example by having improved surfactant efficiency and low tendency to phase-separate internal isomers from solution, especially in presence of water hardness.

Feeds and Streams of the Process

The term "feed" is used herein to identify a material which has not yet been processed by the present process. The term feed" however may also be used when a step which is optional in the present process (e.g., adsorptive separation over 5 Angstrom Ca-zeolite) has been applied to such a material, provided that such treatment occurs before the first essential step of the present process.

The term "stream" is used herein to identify materials which have undergone at least one step of the present process.

The term "branched-enriched stream" herein unless more particularly noted, refers to any processed hydrocarbon fraction containing at least the smaller of the following:

(i) in relative terms, an increase of at least about 10%, preferably at least 100% (that is, a doubling), more preferably a trebling, quadrupling or more, of branched acyclic C8 to about C20 hydrocarbons, compared to a parent fraction or feed which has not been processed in the present process; or (ii) in absolute terms, at least about 5%, preferably 10% or more, of branched acyclic C8 to about C20 hydrocarbons, more preferably of about C10 to about C14 hydrocarbons when the process produces modified alkylbenzenes or modified alkylbenzenesulfonates.

The branched hydrocarbons referred to can be olefinic, paraffinic or mixed olefin/paraffin in any proportion unless otherwise more particularly noted. The branches are preferably monomethyl branches or isolated (non-geminal) dimethyl branches.

The term "linear-enriched stream" herein unless more particularly noted, refers to any processed hydrocarbon fraction which contains a higher percentage by weight of normal (n-) acyclic hydrocarbons than does a parent fraction or feed which has not been processed in the present process.

More particularly, linear-enriched" refers to any processed hydrocarbon fraction containing at least the smaller of the following:

(iii) in relative terms, an increase of at least about 10%, preferably at least 100% (that is, a doubling), more preferably a trebling, quadrupling or more, of linear acyclic C8 to about C20 hydrocarbons, compared to a parent fraction or feed which has not been processed in the present process; or (iv) in absolute terms, at least about 5%, preferably 10% or more, of linear acyclic C8 to about C20 hydrocarbons.

The linear hydrocarbons can be olefinic, paraffinic or mixed olefin/paraffin in any proportion, unless otherwise more particularly identified.

Qualifiers such as "intermediate" when used in connection with a branched-enriched stream are used to identify that the branched-enriched stream to which is being referred has not completed passage through the adsorptive separation stage (a) of the present process. Other qualifiers such as "olefinic" or "paraffinic" may be used to identify whether the stream contains a preponderance of olefinic or of paraffinic hydrocarbons.

Feeds and streams in the present process are further illustrated in the following Table. The numbers in the leftmost column refer to the feeds and streams identified in FIG. 1 through FIG. 7.

| Stream | Stream Type/Name | Exemplary Sources (for Feeds) or compositions (for streams) | Predominant Component(s) |
|---|---|---|---|
| 1 | Hydrocarbon Feed | Jet/Kerosene cuts, preferably from light crudes | b-paraffin/l-paraffin |
| 2 | Branched-enriched Stream (Intermediate) | Mainly branched paraffins; still includes cyclics, aromatics | b-paraffin |
| 3 | Branched-enriched Stream | Mainly methyl branched paraffins | b-paraffin |
| 4 | Branched-enriched Stream (Olefinic) | Mainly methyl branched paraffins; methyl-branched olefins will be present, e.g., at up to about 20% | b-paraffin/b-olefin |
| 5 | Modified Alkylbenzene | Mainly methyl-branched alkylbenzenes | Modified Alkylbenzenes produced by FIG. 1 process with alkylation step |
| 6 | Linear-enriched Stream | Mainly linear paraffins | l-paraffin |
| 7 | Reject Stream (Cyclics/Aromatics) | Cyclics, aromatics, ethyl and higher branched paraffins | |
| 8 | Recycle Stream | Mainly methyl-branched paraffins | b-paraffin |
| 9 | Hydrocarbon Feed | Jet/Kerosene cuts, preferably from light crudes | b-paraffin/l-paraffin |
| 10 | Branched-enriched Stream (Intermediate) | Mainly methyl branched and linear paraffins | b-paraffin/l-paraffin |
| 11 | Branched-enriched Stream | Mainly methyl branched paraffins | b-paraffin |
| 12 | Branched-enriched Stream (Olefinic) | Mainly methyl branched paraffins; methyl-branched olefins must be present, e.g., at up to about 20% | b-paraffin/b-olefin |
| 13 | Modified Alkylbenzene | Mainly methyl-branched alkylbenzenes | Modified Alkylbenzenes produced by FIG. 2 process with alkylation step |
| 14 | Reject Stream (Cyclics/Aromatics | Cyclics, aromatics, ethyl- and higher branched paraffins | |
| 15 | Linear-enriched Stream | Mainly linear paraffins | l-paraffin |
| 16 | Recycle Stream | Mainly methyl-branched paraffins | |
| 17 | Hydrocarbon Feed | Jet/Kerosene cuts, preferably from light crudes | b-paraffin/l-paraffin |
| 18 | Branched-enriched Stream | Mainly methyl branched and linear paraffins | b-paraffin/l-paraffin |
| 19 | Branched-enriched Stream (Olefinic) | Mainly methyl-branched and linear paraffins; must have some linear and methyl branched olefins | b-paraffin/l-paraffin/b-olefin/l-olefin |
| 20 | Linear and Modified Alkylbenzene | Mainly methyl-branched and linear alkylbenzenes | Linear and Modified Alkylbenzene mixture produced by FIG. 3 process |
| 21 | Reject Stream | Cyclics; aromatics, ethyl and higher branched paraffins | |
| 22 | Recycle Stream | Mainly methyl-branched and linear paraffins | |
| 23 | Hydrocarbon Feed | Mixture of branched paraffins and cyclics and aromatics, | b-paraffin |

-continued

| Stream | Stream Type/ Name | Exemplary Sources (for Feeds) or compositions (for streams) | Predominant Component(s) |
|---|---|---|---|
| | | sourced from conventional LAB plant effluent, e.g., MOLEX ® effluent. | |
| 24 | Branched-enriched Stream | Mainly methyl branched paraffins | b-paraffin |
| 25 | Branched-enriched Stream (Olefinic) | Mainly methyl branched paraffins; methyl-branched olefins must be present, e.g., at up to about 20% | b-paraffin/b-olefin |
| 26 | Modified Alkylbenzene | Mainly methyl-branched alkylbenzenes | Modified Alkylbenzenes produced by FIG. 4 process |
| 27 | Reject Stream | Cyclics, aromatics, ethyl and higher branched paraffins | |
| 28 | Recycle Stream | Mainly methyl-branched paraffins | |
| 29 | Hydrocarbon Feed | F.T. gasoline, higher cuts; crackate from slack wax; crackate from Flexicoker or Fluidcoker | b-olefin/l-olefin/b-paraffin/l-paraffin |
| 30 | Branched-enriched Stream (Intermediate) | Mainly methyl-branched and linear olefins; usually have some linear and methyl branched paraffins | b-olefin/l-olefin/b-paraffin/l-paraffin |
| 31 | Branched-enriched Stream | Mainly methyl branched olefins and methyl branched paraffins; variable ratio | b-olefin/b-paraffin |
| 32 | Branched-enriched Stream (Olefinic) | Mainly methyl branched paraffins; methyl branched olefins will be present, e.g., at up to 20% | b-paraffin/b-olefin |
| 33 | Modified Alkylbenzene | Mainly methyl-branched alkylbenzenes | Modified Alkylbenzenes produced by FIG. 5 process |
| 34 | Reject Stream (Cyclics/Aromatics) | Cyclics, aromatics, ethyl- and higher branched paraffins | |
| 35 | Linear-enriched Stream (includes Cyclics/Aromatics) | Mainly linear olefins and linear paraffins | l-olefin/l-paraffin |
| 36 | Recycle Stream | Mainly methyl-branched paraffins | |
| 37 | Hydrocarbon Feed | F.T. gasoline, higher cuts; crackate from slack wax; crackate from Flexicoker or Fluidcoker | b-olefin/l-olefin/b-paraffin/l-paraffin |
| 38 | Branched-enriched Stream (Intermediate) | Branched olefins, branched paraffins, cyclics and aromatics | b-olefin/b-paraffin |
| 39 | Branched-enriched Stream | Mainly methyl branched olefins and methyl branched paraffins; variable ratio | b-olefin/b-paraffin |
| 40 | Branched-enriched Stream (Olefinic) | Mainly methyl branched paraffins; methyl branched olefins will be present, e.g., at up to 20% | b-paraffin/b-olefin |
| 41 | Modified Alkylbenzene | Mainly methyl-branched alkylbenzenes | Modified Alkylbenzenes produced by FIG. 6 process |
| 42 | Linear-enriched Stream | Mainly linear olefins and linear paraffins | l-olefin/l-paraffin |
| 43 | Reject Stream (Cyclics/Aromatics) | Cyclics, aromatics, ethyl- and higher branched paraffins | |
| 44 | Recycle Stream | Mainly methyl-branched paraffins | |
| 45 | Hydrocarbon Feed | F.T. gasoline, higher cuts; crackate from slack wax; crackate from Flexicoker or Fluidcoker | b-olefin/l-olefin/b-paraffin/l-paraffin |
| 46 | Branched-enriched Stream | Mainly methyl-branched and linear olefins; usually have some linear and methyl branched paraffins | b-olefin/l-olefin/b-paraffin/l-paraffin |
| 47 | Branched-enriched Stream (Olefinic) | Mainly linear and methyl-branched paraffins; will have some linear and methyl branched olefins | b-paraffin/l-paraffin/b-olefin/l-olefin |

-continued

| Stream | Stream Type/ Name | Exemplary Sources (for Feeds) or compositions (for streams) | Predominant Component(s) |
|---|---|---|---|
| 48 | Modified Alkylbenzene | Mainly methyl-branched and linear alkylbenzenes | Modified Alkylbenzenes produced by FIG. 7 process |
| 49 | Reject Stream (Cyclics/ Aromatics) | Cyclics, aromatics, ethyl- and higher branched paraffins | |
| 50 | Recycle Stream | Mainly methyl-branched and linear paraffins | |

The hydrocarbon feeds exemplified in the table hereinabove should of course be viewed as illustrative and not limiting of the present invention. Any other suitable hydrocarbon feed may be used. For example, crackates of petroleum waxes. These waxes are from lube oil distillate fractions and melt in the relatively low range up to about 72 deg. C, e.g., in the range from about 50 deg. C to about 70 deg. C and contain from about 18 to about 36 carbon atoms. Such waxes preferably contain 50% to 90% normal alkanes and 10% to 50% of monomethyl branched alkanes and low levels of various cyclic alkanes. Such crackate feeds are especially useful in alternate embodiments of the invention as further described in detail hereinafter, and are described in "Chemical Economics Handbook", published by SRI, Menlo Park, Calif. See, for example, "Waxes", S595.5003 L, published 1995. Paraffin waxes are also described in Kirk Othmer's Encyclopedia of Chemical Technology, $3^{rd}$. Edition (1984), Volume 24. See "Waxes" at page 473. Any equivalent alternative hydrocarbon feeds or more preferably shorter-chain equivalents in the C10–C20 range and having appreciable monomethyl-branching in any position on the chain, for example from Fischer-Tropsch synthesis, are also suitable.

Hydrocarbon feeds herein can contain varying amounts of N,O,S impurity. Certain preferred hydrocarbon feeds, especially if derived from sulfur- and/or nitrogen-containing fractions, are desulfurized and/or freed from nitrogenous matter using conventional desulfurization or "de-NOS" technology.

Adsorptive Separation Step(s)

In general, separation techniques in step or steps (a) of the instant process rely on adsorption on porous media and/or use of clathrates. A landmark patent on adsorptive separation is U.S. Pat. No. 2,985,589 which illustrates devices, adsorbent beds and process conditions of temperature and pressure generally suitable for use herein. '589 does not describe critical modifications, especially pore sizes for specific separations and connection of steps, that are part of the present invention.

Adsorptive separation steps herein can, in general, be conducted in the vapor phase or the liquid phase, and may or may not employ any of the commercialized process equipment as identified in the background of the invention.

Porous media used as adsorbents can in general be dried or non-dried. Preferred embodiments include those wherein the adsorbents are dried and contain less than about 2% free moisture.

Any adsorptive separation step according to the present invention may, or may not use a desorbent or displacing agent. In general, any desorption means, such as pressure-swing or other means, can be used. However, preferably such desorbing agent is used, in other words, solvent displacement is a preferred method of desorbing streams from the porous media used herein. Suitable desorbents or displacing agents include a lower-molecular weight n-paraffin such as heptane, octane or the like, or a polar desorbent such as ammonia. It should be understood that, irrespective of their presence, such well-known desorbents, being fully conventional, are not explicitly included in identifying any of the streams or their compositions in the processes herein, and can be recycled at will using desorbent recycle steps not explicity shown in FIGS. 1–7.

In the present process, stage (a) can use a MOLEX® process step of UOP, subject to the difference that the present process must have at least one adsorptive separation using a porous material which has larger pores than the usual 5 Angstrom zeolite as used in linear alkylbenzene manufacture. MOLEX® is discussed in the hereinabove-identified Surfactant Science Series Vol. 56, including for example pages 5–10. Vapor-phase processes such as Union Carbide's IsoSiv process (see the same reference) are also useful but less preferred.

Apparatus and operating conditions for the MOLEX® process in any version used herein are well-known; see, for example the above-identified reference at page 9 showing the process and its various streams including raffinate and absorbent in detail.

Porous Media (Larger-pore Types)

Porous media required in stage (a) herein are larger-pore types. By "larger-pore" is specifically meant porous media having pores large enough to retain mono-methyl-branched linear olefinic or paraffinic hydrocarbons and dimethyl-branched or trimethyl-branched linear olefinic or paraffinic hydrocarbons other than gem-dimethyl hydrocarbons, while being small enough to at least partly exclude gem-dimethyl, ethyl and higher-branched hydrocarbons as well as cyclic (e.g., 5-, 6-membered rings) and aromatic hydrocarbons. Such pore sizes large enough to retain appreciable amounts of methyl-branched hydrocarbons are invariably not used in conventional linear alkylbenzene manufacture and in general are far more rarely used in any commercial processes than are the more familiar 4–5 Angstrom pore size zeolites. The larger-pore porous media are those used in FIGS. 1–7 in the adsorptive separation units marked as "SOR 5/7".

Porous media essential in stage (a) herein accordingly have a minimum pore size larger than the pore size required for selective adsorption of linear acyclic hydrocarbons, i.e., in excess of those used in conventional linear alkylbenzene manufacture, said pore size not exceeding about 20 Angstroms, more preferably not exceeding about 10 Angstroms and very preferably, from above about 5 Angstroms to about 7 Angstroms on average. When specifying minimum pore size for the so-called "larger-pore" porous materials herein, it should be recognized that such materials often have elliptical pores, for example SAPO-11 has a pore size of 4.4 by 6.7 Angstrom. (5.55 Angstrom average). See S.

Miller, Microporus Materials, Vol. 2., pages 439–449 (1994). When comparing such a material with a "smaller-pore" zeolite such as a 4–5 Angstrom uniform-pore zeolite, the convention herein is to look to the average of elliptical dimensions or the larger elliptical dimension—in any event not to the smaller elliptical dimension—when making the size comparison. Thus the SAPO-11 material herein by definition has a pore size larger than a 5 Angstrom, uniform-pore zeolite.

Porous media having the larger pores essential in stage (a) herein can be either zeolites (aluminosilicates) or non-zeolites.

Suitable non-zeolites include the silicoaluminophosphates, especially SAPO-11 though other silicoaluminophosphates can be used if the average pore size is greater than about 5 Angstroms or if elliptical pores are present with at least one elliptical dimension above 5 Angstroms.

Another technique suitable for adsorptive separation herein is absorption using pyrolyzed poly(vinylidene chloride) i.e., pyrolyzed SARAN, for example manufactured according to Netherlands Application NL 7111508 published Oct. 25, 1971. Preferred materials have sieve diameter of from 4–7 Angstrom. When using such material as the essential adsorbent, a pore size above about 5 Angstrom will be used.

Use of Organometallic-grafted Mordenites and Other Grafted Zeolites as Porous Media in Stage (a)

The present invention also includes especially useful embodiments wherein the adsorptive separations of stage (a) comprise at least one separation step using an organometallic-grafted mordenite. Especially suitable as the "large-pore" porous media herein are grafted mordenites such as a tin-grafted mordenite. Likewise, and more generally, the invention encompasses a method comprising use of a grafted mordenite for manufacturing detergent surfactants and any of the corresponding surfactants and consumer products produced by use of these specific porous media in any of the above-defined processes. See EP 559, 510 A 9/8/93 incorporated by reference in its entirety. The practitioner will select those grafted mordenites of EP 559, 510 which are clearly identifiable from the Examples thereof to be best suited for separations of linear and monomethyl-branched hydrocarbons from gem-dimethyl and polymethyl hydrocarbons.

Other grafted zeolites useful as the porous media herein include those of U.S. Pat. No. 5,326,928, also incorporated by reference in its entirety. In such embodiments of the instant invention, it is especially preferred to integrate into a single process the use both of the above-identified grafted mordenite in stage (a), and the use of an at least partially dealuminized H-mordenite in step (c), the alkylation step defined elsewhere herein.

On this basis, using the terminology of U.S. Pat. No. 5,326,928 to describe the process module containing the grafted component and combining therewith the preferred alkylation step as defined herein, the present invention also encompasses a process for making modified alkylbenzenes and/or modified alkylbenzenesulfonates, said process comprising: (a) at least one stage of separating aliphatic paraffins having varying degrees of branching in a hydrocarbon charge containing molecules of 9 to 14 carbon atoms into at least one first effluent comprising less branched (linear and monomethyl, optionally some dimethyl-branched) paraffins and at least one second effluent comprising more branched parafins (trimethyl and higher-branched paraffins and optionally cyclic and/or aromatic impurities), said separa- tion comprising contacting the hydrocarbon charge with at least one adsorbent bed comprising at least one microporous solid (as defined in U.S. Pat. No. 5,326,928) having grafted in the pores thereof an organometallic compound of a quantity and shape sufficient to yield pores selective for entry of the less branched paraffins but not the more branched paraffins; (b) at least one stage of alkylating a less branched effluent of stage (a), preferably in an alkylation having internal isomer selectivity of from 0 to 40, and more preferably still, using an at least partially dealuminized, at least partially acidic H-mordenite as catalyst; and (c) at least one stage of sulfonating the product of stage (b) using any conventional sulfonating agent. The resulting modified alkylbenzenesulfonic acid can be neutralized and incorporated into cleaning products as taught elsewhere herein.

In stage (a) of the present process, there is a preference to use zeolites or other porous media in such a form that they do not actively promote chemical reactions of the feedstock., e.g., cracking, polymerization. Thus, acidic mordenite is preferably avoided in stage (a). See in contrast alkylation catalysts hereinafter, in which at least partial acid-form is preferred.

Porous Media (Smaller-pore Types)

Smaller-pore zeolites optionally useful in stage (a) herein, for example those used in processes such as those of the adsorptive separation unit identified as "SOR 4/5" in FIGS. 1, 2, 5, 6, are those which selectively adsorb linear hydrocarbons and which do not adsorb methyl-branched hydrocarbons appreciably. Such porous materials are well-known and include, for example, Calcium Zeolites with 4–5 Angstrom pores. Such materials are further illustrated in U.S. Pat. No. 2,985,589 and are those in current commercial use for manufacture of linear alkylbenzenes.

Clathration

Urea clathration can also be used herein in stage (a) for separating n-paraffins from branched paraffins, as is well known in the art. See, for example, Surfactant Science Series, Marcel Dekker, N.Y., 1996, Vol. 56, pages 9–10 and references therein. See also "Detergent Manufacture Including Zeolite Builders and other New Materials, Ed. Sittig., Noyes Data Corp., 1979, pages 25–30 and especially U.S. Pat. No. 3,506,569 incorporated in its entirety which uses solid urea and no chlorocarbon solvents. More generally but less preferably, processes according to U.S. Pat. No. 3,162, 627 may be used.

Dehydrogenation

In general, dehydrogenation of the olefin or olefin/paraffin mixtures in the instant process can be accomplished using any of the well-known dehydrogenation catalyst systems, including those described in the Surfactant Science Series references cited in the background as well as in "Detergent Manufacture Including Zeolite Builders and Other New Materials", Ed. Sittig, Noyes Data Corp., New Jersey, 1979 and other dehydrogenation catalyst systems, for example those commercially available though UOP Corp. Dehydrogenation can be conducted in presence of hydrogen gas and commonly a precious metal catalyst (e.g., DeH-5, DeH-7, DeH-9 available from UOP) is present though alternatively non-hydrogen, precious-metal free dehydrogenation systems such as a zeolite/air system can be used with no precious metals present.

More specifically, dehydrogenation catalysts useful herein include a catalyst supported on Sn-containing alumina and having Pt: 0.16%, Ir: 0.24%, Sn: 0.50%, and Li: 0.54% as described in U.S. Pat. No. 5,012,027 incorporated by reference. This catalyst, when contacted with a C9–C14 paraffin mixture (believed to be linear) at 500 deg. C and 0.68 atm. produces olefinic products (38 h on stream) with 90.88% selectivity and 11.02% conversion and is believed to be very suitable for at least partially dehydrogenating branched-enriched streams of paraffins herein. See also U.S. Pat. No. 4,786,625; EP 320,549 A1 6/21/89; Vora et al., Chem. Age India (1986), 37(6), 415–18;

As noted supra, dehydrogenation can be complete or partial, more typically partial. When partial, this step forms a mixture of olefin (e.g., about 10% though this figure is illustrative and should not be taken as limiting) and the balance unreacted paraffin. Such mixture is a suitable feed for the alkylation step of the instant process.

Other useful dehydrogenation systems readily adapted into the present invention include those of U.S. Pat. No. 4,762,960 incorporated by reference which discloses a Pt-group metal containing dehydrogenation catalyst having a modifier metal selected from the group consisting of Sn, Ge, Re and their mixtures, an alkali metal, an alkaline earth metal or their mixtures, and a particularly defined refractory oxide support.

Alternative dehydrogenation catalysts and conditions useful herein include those of U.S. Pat. No. 4,886,926 and of U.S. Pat. No. 5,536,695.

Alkylation

Important embodiments of the present invention further include alkylation, which takes place after delinearization by separative enrichment of lightly branched paraffin and at least partial dehydrogenation of the delinearized olefin or olefin/paraffin mixtures. Alkylation is conducted with an aromatic hydrocarbon selected from benzene, toluene and mixtures thereof.

Internal Isomer Selectivity and Selection of Alkylation Step

Preferred embodiments of the present processes require an alkylation step having internal isomer selectivity in the range from 0 to 40, preferably from 0 to 20, more preferably still from 0 to 10. The Internal Isomer Selectivity or "IIS" as defined herein is measured for any given alkylation process step by conducting a test alkylation of benzene by 1-dodecene at a molar ratio of 10:1. The alkylation is conducted in the presence of an alkylation catalyst to a conversion of dodecene of at least 90% and formation of monophenyldodecanes of at least 60%. Internal isomer selectivity is then determined as:

$$IIS = 100 * \left(1 - \frac{\text{amount of terminal phenyldodecanes}}{\text{amount of total phenyldodecanes}}\right)$$

wherein amounts are amounts of the products by weight; the amount of terminal phenyldodecanes is the amount of the sum of 2-phenyldodecane and 3-phenyldodecane and the amount of total phenyldodecanes is the amount of the sum of 2-phenyldodecane and 3-phenyldodecane and 4-phenyldodecane and 5-phenyldodecane and 6-phenyldodecane and wherein said amounts are determined by any known analytical technique for alkylbenzenesulfonates such as gas chromatography. See Analytical Chemistry, Nov. 1983, 55 (13), 2120–2126, Eganhouse et al, "Determination of long-chain alkylbenzenes in environmental samples by argentation thin-layer chromatography—high resolution gas chromatography and gas chromatography/mass spectrometry". In computing IIS according to the above formula, the amounts are divided before subtracting the result from 1 and multiplying by 100. It should of course be understood that the specific alkenes used to characterize or test any given alkylation step for suitability are reference materials permitting a comparison of the alkylation step herein with known alkylation steps as used in making linear alkylbenzenes and permitting the practitioner of the invention to decide if a given known alkylation step is, or is not, useful in the context of the series of process steps constituting the present invention. In the process of the invention as practiced, the hydrocarbon feedstock for alkylation actually used is of course that which is specified on the basis of the preceding process steps. Also to be noted, all the current commercial processes for LAS manufacture are excluded from preferred embodiments of the present invention solely on the basis of the IIS for the alkylation step. For example, LAS processes based on aluminum chloride, HF and the like all have IIS outside of the range specified for the instant process. In contrast, a few alkylation steps described in the literature but not currently applied in commercial alkylbenzenesulfonate production do have suitable IIS and are useful herein.

The better to assist the practitioner in determining IIS and in deciding whether a given alkylation process step is suitable for the purposes of the present invention, the following are more particular examples of IIS determination.

As noted, test alkylation of benzene by 1-dodecene is conducted at a mole ratio of 10:1 benzene to 1-dodecene and the alkylation is conducted in the presence of an alkylation catalyst to a conversion of dodecene of at least 90% and formation of monophenyldodecanes of at least 60%. The alkylation test must in general be conducted in a reaction time of less than 200 hours and at a reaction temperature of from about −15° C. to about 500° C., preferably from about 20° C. to 500° C. Pressure and catalyst concentration relative to 1-dodecene can vary widely. No solvent other than benzene is used in the test alkylation. The process conditions used to determine the IIS for the catalyst or alkylation step in question can be based on the literature. The practitioner will use generally appropriate conditions based on a large body of well-documented data for alkylations. For example, appropriate process conditions to determine if an $AlCl_3$ alkylation can be used herein are exemplified by a reaction of 5 mole % $AlCl_3$ relative to 1-dodecene at 20–40° C. for 0.5–1.0 hour in a batch reactor. Such a test demonstrates that an $AlCl_3$ alkylation step is unsuitable for use in the present process. An IIS of about 48 should be obtained. In another example, an appropriate test of alkylation using HF as a catalyst should give an IIS of about 60. Thus, neither $AlCl_3$ alkylation nor HF alkylation is within the scope of this invention. For a medium-pore zeolite such as a dealuminized mordenite, process conditions suitable for determining IIS are exemplified by passing 1-dodecene and benzene at a mole ratio of 10:1 across the mordenite catalyst at a WHSV of 30 $Hr^{-1}$ at a reaction temperature of about 200° C. and a pressure of about 200 psig which should give an IIS of about 0 for the mordenite catalyst. The temperatures and pressures for the exemplary mordenite alkylation test (see also the detailed examples of the instant process hereinafter) are expected to be more generally useful for testing zeolites and other shape-selective alkylation catalysts. Using a catalyst such as H-ZSM-4 one should obtain an IIS of about 18. Clearly both the dealuminized mordenite and H-ZSM-4 catalyzed alkylations give acceptable IIS for the invention, with the mordenite being superior.

Without intending to be limited by theory, it is believed that the low-IIS alkylation step practiced using H-mordenites herein is capable both of alkylating benzene with the branched-enriched hydrocarbon, but very usefully also of scrambling the position of a methyl branch attached to the hydrocarbon chain.

Alkylation Catalyst

Accomplishing the required IIS in the alkylation process step is made possible by a tightly controlled selection of alkylation catalysts. Numerous alkylation catalysts are readily determined to be unsuitable. Unsuitable alkylation catalysts include the DETAL® process catalysts, aluminum chloride, HF, HF on zeolites, fluoridated zeolites, non-acidic calcium mordenite, and many others. Indeed no alkylation catalyst currently used for alkylation in the commercial production of detergent linear alkylbenzenesulfonates has yet been found suitable.

In contrast, suitable alkylation catalyst herein is selected from shape-selective moderately acidic alkylation catalysts, preferably zeolitic. The zeolite in such catalysts for the alkylation step (step (b)) is preferably selected from the group consisting of mordenite, ZSM-4, ZSM-12, ZSM-20, offretite, gmelinite and zeolite beta in at least partially acidic form. More preferably, the zeolite in step (b) (the alkylation step) is substantially in acid form and is contained in a catalyst pellet comprising a conventional binder and further wherein said catalyst pellet comprises at least about 1%, more preferably at least 5%, more typically from 50% to about 90%, of said zeolite.

More generally, suitable alkylation catalyst is typically at least partially crystalline, more preferably substantially crystalline not including binders or other materials used to form catalyst pellets, aggregates or composites. Moreover the catalyst is typically at least partially acidic. Fully exchanged Ca-form mordenite, for example, is unsuitable whereas H-form mordenite is suitable. This catalyst is useful for the alkylation step identified as step (b) in the claims hereinafter: these correspond to Step 7 in FIG. 1.

The pores characterizing the zeolites useful in the present alkylation process may be substantially circular, such as in cancrinite which has uniform pores of about 6.2 angstroms, or preferably may be somewhat elliptical, such as in mordenite. It should be understood that, in any case, the zeolites used as catalysts in the alkylation step of the present process have a major pore dimension intermediate between that of the large pore zeolites, such as the X and Y zeolites, and the relatively small pore size zeolites ZSM-5 and ZSM-11, and preferably between about 6 A and about 7 A. Indeed ZSM-5 has been tried and found inoperable in the present invention. The pore size dimensions and crystal structures of certain zeolites are specified in ATLAS OF ZEOLITE STRUCTURE TYPES by W. M. Meier and D. H. Olson, published by the Structure Commission of the International Zeolite Association (1978 and more recent editions) and distributed by Polycrystal Book Service, Pittsburgh, Pa.

The zeolites useful in the alkylation step of the instant process generally have at least 10 percent of the cationic sites thereof occupied by ions other than alkali or alkaline-earth metals. Typical but non-limiting replacing ions include ammonium, hydrogen, rare earth, zinc, copper and aluminum. Of this group, particular preference is accorded ammonium, hydrogen, rare earth or combinations thereof In a preferred embodiment, the zeolites are converted to the predominantly hydrogen form, generally by replacement of the alkali metal or other ion originally present with hydrogen ion precursors, e.g., ammonium ions, which upon calcination yield the hydrogen form. This exchange is conveniently carried out by contact of the zeolite with an ammonium salt solution, e.g., ammonium chloride, utilizing well known ion exchange techniques. In certain preferred embodiments, the extent of replacement is such as to produce a zeolite material in which at least 50 percent of the cationic sites are occupied by hydrogen ions.

The zeolites may be subjected to various chemical treatments, including alumina extraction (dealumination) and combination with one or more metal components, particularly the metals of Groups IB, III, IV, VI, VII and VIII. It is also contemplated that the zeolites may, in some instances, desirably be subjected to thermal treatment, including steaming or calcination in air, hydrogen or an inert gas, e.g. nitrogen or helium.

A suitable modifying treatment entails steaming of the zeolite by contact with an atmosphere containing from about 5 to about 100 percent steam at a temperature of from about 250 degree(s) to 1000 degree(s) C. Steaming may last for a period of between about 0.25 and about 100 hours and may be conducted at pressures ranging from sub-atmospheric to several hundred atmospheres.

In practicing the desired alkylation step of the instant process, it may be useful to incorporate the above-described intermediate pore size crystalline zeolites in another material, e.g., a binder or matrix resistant to the temperature and other conditions employed in the process. Such matrix materials include synthetic or naturally occurring substances as well as inorganic materials such as clay, silica, and/or metal oxides. Matrix materials can be in the form of gels including mixtures of silica and metal oxides. The latter may be either naturally occurring or in the form of gels or gelatinous precipitates. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the intermediate pore size zeolites employed herein may be compounded with a porous matrix material, such as alumina, silica-alumina, silica-magnesia, silica-zirconia, silica-thoria, silica-beryllia, and silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely, with the zeolite content ranging from between about 1 to about 99 percent by weight and more usually in the range of about 5 to about 80 percent by weight of the composite.

A group of zeolites which includes some useful for the alkylation step herein have a silica: alumina ratio of at least 10:1, preferably at least 20:1. The silica:alumina ratios referred to in this specification are the structural or framework ratios, that is, the ratio for the $SiO_4$ to the $AlO_4$ tetrahedra. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as the dealuminization methods described below which result in the presence of ionic aluminum free of the zeolite structure are employed. Due care should therefore be taken to ensure that the framework silica: alumina ratio is correctly determined.

Zeolite beta suitable for use herein (but less preferred than H-mordenite) is disclosed in U.S. Pat. No. 3,308,069 to which reference is made for details of this zeolite and its preparation. Such a zeolite in the acid form is also commercially available as Zeocat PB/H from Zeochem.

When the zeolites have been prepared in the presence of organic cations they are catalytically inactive, possibly because the intracrystalline free space is occupied by organic cations from the forming solution. They may be activated by heating in an inert atmosphere at 540 degree(s) C. for one hour, for example, followed by base exchange with ammonium salts followed by calcination at 540 degree(s) C. in air. The presence of organic cations in the forming solution may not be absolutely essential to the formation of the zeolite; but it does appear to favor the formation of this special type of zeolite. Some natural zeolites may sometimes be converted to zeolites of the desired type by various activation procedures and other treatments such as base exchange, steaming, alumina extraction and calcination. The zeolites preferably have a crystal framework density, in the dry hydrogen form, not substantially below about 1.6 g·cm–3. The dry density for known structures may be calculated from the number of silicon plus aluminum atoms per 1000 cubic Angstroms, as given, e.g., on page 19 of the article on Zeolite Structure by W. M. Meier included in "Proceedings of the Conference on Molecular Sieves, London, April 1967", published by the Society of Chemical Industry, London, 1968. Reference is made to this paper for a discussion of the crystal framework density. A further discussion of crystal framework density, together with values for some typical zeolites, is given in U.S. Pat. No. 4,016,218, to which reference is made. When synthesized in the alkali metal form, the zeolite is conveniently converted to the hydrogen form, generally by intermediate formation of the ammonium form as a result of ammonium ion exchange and calcination of the ammonium form to yield the hydrogen form. It has been found that although the hydrogen form of the zeolite catalyzes the reaction successfully, the zeolite may also be partly in the alkali metal form.

EP 466,558 describes an acidic mordenite type alkylation catalyst also of possible use herein having overall Si/Al atomic ratio of 15–85 (15–60), Na weight content of less than 1000 ppm (preferably less than 250 ppm), having low or zero content of extra-network Al species, and an elementary mesh volume below 2,760 nm3.

U.S. Pat. No. 5,057,472 useful for preparing alkylation catalysts herein relates to concurrent dealumination and ion-exchange of an acid-stable Na ion-containing zeolite, preferably mordenite effected by contact with a 0.5–3 (preferably 1–2.5) M HNO3 solution containing sufficient NH4NO3 to fully exchange the Na ions for NH4 and H ions. The resulting zeolites can have an SiO2: Al2O3 ratio of 15–26 (preferably 17–23):1 and are preferably calcined to at least partially convert the NH4/H form to an H form. Optionally, though not necessarily particularly desirable in the present invention, the catalyst can contain a Group VIII metal (and optionally also an inorganic oxide) together with the calcined zeolite of '472.

Another acidic mordenite catalyst useful for the alkylation step herein is disclosed in U.S. Pat. No. 4,861,935 which relates to a hydrogen form mordenite incorporated with alumina, the composition having a surface area of at least 580 m2/g. Other acidic mordenite catalysts useful for the alkylation step herein include those described in U.S. Pat. No. 5,243,116 and U.S. Pat. No. 5,198,595. Yet another alkylation catalyst useful herein is described in U.S. Pat. No. 5,175,135 which is an acid mordenite zeolite having a silica/alumina molar ratio of at least 50:1, a Symmetry Index of at least 1.0 as determined by X-ray diffraction analysis, and a porosity such that the total pore volume is in the range from about 0.18 cc/g to about 0.45 cc/g and the ratio of the combined meso- and macropore volume to the total pore volume is from about 0.25 to about 0.75.

Particularly preferred alkylation catalysts herein include the acidic mordenite catalysts Zeocat™ FM-8/25H available from Zeochem; CBV 90 A available from Zeolyst International, and LZM-8 available from UOP Chemical Catalysts.

Most generally, any alkylation catalyst may be used herein provided that the alkylation step meets the internal isomer selectivity requirements identified supra.

Most generally, any alkylation catalyst may be used herein provided that the alkylation step meets the internal isomer selectivity requirements identified supra.

Distillation of Modified Alkylbenzenes

Optionally, depending on feedstock and the precise sequence of steps used, the present process can include distillation of modified alkylbenzenes, for example to remove unreacted starting materials, paraffins, excesses of benzene and the like. Any conventional distillation apparatus can be used. The general practice is similar to that used for distillation of commercial linear alkylbenzenes (LAB). Suitable distillation steps are described in the hereinabove-referenced Surfactant Science Series review of alkylbenzenesulfonate manufacture.

Sulfonation and Workup

In general, sulfonation of the modified alkylbenzenes in the instant process can be accomplished using any of the well-known sulfonation systems, including those described in the hereinabove-referenced volume "Detergent Manufacture Including Zeolite Builders and Other New Materials" as well as in the hereinabove-referenced Surfactant Science Series review of alkylbenzenesulfonate manufacture. Common sulfonation systems include sulfuric acid, chlorosulfonic acid, oleum, sulfur trioxide and the like. Sulfur trioxide/air is especially preferred. Details of sulfonation using a suitable air/sulfur trioxide mixture are provided in U.S. Pat. No. 3,427,342, Chemithon. Sulfonation processes are further extensively described in "Sulfonation Technology in the Detergent Industry", W. H. de Groot, Kluwer Academic Publishers, Boston, 1991.

Any convenient workup steps may be used in the present process. Common practice is to neutralize after sulfonation with any suitable alkali. Thus the neutralization step can be conducted using alkali selected from sodium, potassium, ammonium, magnesium and substituted ammonium alkalis and mixtures thereof Potassium can assist solubility, magnesium can promote soft water performance and substituted ammonium can be helpful for formulating specialty variations of the instant surfactants. The invention encompasses any of these derivative forms of the modified alkylbenzenesulfonate surfactants as produced by the present process and their use in consumer product compositions.

Alternately the acid form of the present surfactants can be added directly to acidic cleaning products, or can be mixed with cleaning ingredients and then neutralized.

Post-alkylation Steps

As noted, the process herein includes embodiments having steps that take place subsequent to the alkylation step (c). These steps preferably include (d) sulfonating the product of step (c); and one or more steps selected from (e) neutralizing the product of step (d); and (f) mixing the product of step (d) or (e) with one or more cleaning product adjunct materials; thereby forming a cleaning product.

Blended Embodiments

In one preferred embodiment, prior to said sulfonation step, modified alkylbenzene which is the product of said step (c) is blended with a linear alkylbenzene produced by a conventional process. In another such embodiment, in any step subsequent to said sulfonation step, modified alkylbenzene sulfonate which is the product of said step (d) is blended with a linear alkylbenzene produced by a conventional process. In these blended embodiments, a preferred process has a ratio of modified alkylbenzene to linear alkylbenzene of from about 10:90 to about 50:50.

Other Process Embodiments

The present invention also encompasses a process for beneficiating an effluent stream from the manufacture of linear alkylbenzenesulfonate surfactants useful in cleaning products, said process comprising (i) at least partially separating an isoparaffin into a normal paraffin enriched stream and an effluent stream having the form of an isoparaffin (especially methyl branched paraffin) enriched stream comprising at least about 10% isoparaffin and having molecular weight of at least about 128 and no more than about 282 wherein said separation comprises at least one step selected from clathration by means of urea and separation by means of absorption and wherein said steps are integral in a process for linear alkylbenzene manufacture; (ii) at least partially further enriching the isoparaffin content of said effluent stream by at least one step selected from urea clathration and adsorptive separation; wherein said step is additional to and follows step (i); and (iii) a step of at least partially dehydrogenating the isoparaffin enriched stream of said step (ii).

More generally, it is contemplated that the hydrocarbons produced herein can be useful not only in modified alkylbenzenesulfonate surfactants as nonlimitingly illustrated herein but also in modified surfactants other than alkylbenzenesulfonates (such as alkyl sulfates). Thus the present invention also encompasses a process for beneficiating a branched paraffinic effluent stream comprising (i) at least partially separating an isoparaffin into a normal paraffin enriched stream and an effluent stream having the form of an isoparaffin enriched stream comprising at least about 10% isoparaffin wherein said separation comprises at least one step selected from clathration by means of urea and separation by means of absorption; (ii) at least partially further enriching the isoparaffin content of said effluent stream by at least one step selected from urea clathration and adsorptive separation; wherein said step is additional to and follows step (i); and (iii) a step of at least partially dehydrogenating the isoparaffin enriched stream of said step (ii).

In such embodiments, the isoparaffin enriched stream may vary from about C10 to about C20 in overall carbon content and the nonlinear fraction of said enriched stream comprises an average of from about one to about two methyl side chains other than terminal methyl side-chains per molecule and further, the nonlinear fraction of said enriched stream preferably comprises less than about 30%, more preferably less than about 10%, more preferably still less than about 1% of molecules having quaternary carbon atoms and less than 50%, preferably less than about 10%, more preferably less than about 1% of molecules having gem-dimethyl substitution.

Cleaning Product Embodiments

Cleaning product embodiments of the present invention include laundry detergents, dishwashing detergents, hard surface cleaners and the like. In such embodiments, the content of modified alkylbenzenesulfonate produced by the instant process is from about 0.1% to about 99.9%, typically from about 1% to about 50%, and the composition further comprises from about 0.1% to about 99.9%, typically from about 1% to about 50%, of cleaning product adjunct materials such as cosurfactants, builders, enzymes, bleaches, bleach promoters, activators or catalysts, and the like.

The present invention also encompasses a cleaning product formed by the instant process comprising:
- (a) from about 0.1% to about 99.8%, more typically up to about 50%, of modified alkylbenzenesulfonate surfactant as prepared herein and
- (b) from about 0.00001%, more typically at least about 1%, to about 99.9% of one or more of said cleaning product adjunct materials.

Adjunct materials can vary widely and accordingly can be used at widely ranging levels. For example, detersive enzymes such as proteases, amylases, cellulases, lipases and the like as well as bleach catalysts including the macrocyclic types having manganese or similar transition metals all useful in laundry and cleaning products can be used herein at very low, or less commonly, higher levels.

Other cleaning product adjunct materials suitable herein include bleaches, especially the oxygen bleach types including activated and catalyzed forms with such bleach activators as nonanoyloxybenzenesulfonate and/or tetraacetylethylenediamine and/or any of its derivatives or derivatives of phthaloylimidoperoxycaproic acid or other imido- or amido-substituted bleach activators including the lactam types, or more generally any mixture of hydrophilic and/or hydrophobic bleach activators (especially acyl derivatives including those of the C6–C16 substituted oxybenzenesulfonates); preformed peracids related to or based on any of the hereinbefore mentioned bleach activators, builders including the insoluble types such as zeolites including zeolites A, P and the so-called maximum aluminum P as well as the soluble types such as the phosphates and polyphosphates, any of the hydrous, water-soluble or water-insoluble silicates, 2,2'-oxydisuccinates, tartrate succinates, glycolates, NTA and many other ethercarboxylates or citrates, chelants including EDTA, S,S'-EDDS, DTPA and phosphonates, water-soluble polymers, copolymers and terpolymers, soil release polymers, cosurfactants including any of the known anionic, cationic, nonionic or zwitterionic types, optical brighteners, processing aids such as crisping agents and/fillers, solvents, antiredeposition agents, silicone/silica and other suds suppressors, hydrotropes, perfumes or pro-perfumes, dyes, photobleaches, thickeners, simple salts and alkalis such as those based on sodium or potassium including the hydroxides, carbonates, bicarbonates and sulfates and the like. When combined with the modified alkylbenzenesulfonate surfactants of the instant process, any of the anhydrous, hydrous, water-based or solvent-borne cleaning products are readily accessible as granules, tablets, powders, flakes, gels, extrudates, pouched or encapsulated forms or the like. Accordingly the present invention also includes the various cleaning products made possible or formed by any of the processes described. These may be used in discrete dosage forms, used by hand or by machine, or may be continuously dosed into all suitable cleaning appliances or delivery devices.

Cleaning Products in Detail

References cited herein are incorporated by reference. The surfactant compositions prepared by the processes of the present invention can be used in a wide range of consumer cleaning product compositions including powders, granules, gels, pastes, tablets, pouches, bars, types delivered in dual-compartment containers, spray or foam detergents and other homogeneous or multiphasic consumer cleaning product forms. They can be used or applied by hand and/or can be applied in unitary or freely alterable dosage, or by automatic dispensing means, or are useful in appliances such as washing-machines or dishwashers or can be used in institutional cleaning contexts, including for example, for personal cleansing in public facilities, for bottle washing, for surgical instrument cleaning or for cleaning electronic components. They can have a wide range of pH, for example from about 2 to about 12 or higher, and they can have a wide range of alkalinity reserve which can include very high alkalinity reserves as in uses such as drain unblocking in which tens of grams of NaOH equivalent can be present per 100 grams of formulation, ranging through the 1–10 grams of NaOH equivalent and the mild or low-alkalinity ranges of liquid hand cleaners, down to the acid side such as in acidic hard-surface cleaners. Both high-foaming and low-foaming detergent types are encompassed.

Consumer product cleaning compositions are described in the "Surfactant Science Series", Marcel Dekker, New York, Volumes 1–67 and higher. Liquid compositions in particular are described in detail in the Volume 67, "Liquid Detergents", Ed. Kuo-Yann Lai, 1997, ISBN 0-8247-9391-9 incorporated herein by reference. More classical formulations, especially granular types, are described in "Detergent Manufacture including Zeolite Builders and Other New Materials", Ed. M. Sittig, Noyes Data Corporation, 1979 incorporated by reference. See also Kirk Othmer's Encyclopedia of Chemical Technology.

Consumer product cleaning compositions herein nonlimitingly include:

Light Duty Liquid Detergents (LDL): these compositions include LDL compositions having surfactancy improving magnesium ions (see for example WO 97/00930 A; GB 2,292,562 A; U.S. Pat. No. 5,376,310; U.S. Pat. No. 5,269,974; U.S. Pat. No. 5,230,823; U.S. Pat. No. 4,923,635; U.S. Pat. No. 4,681,704; U.S. Pat. No. 4,316,824; U.S. Pat. No. 4,133,779) and/or organic diamines and/or various foam stabilizers and/or foam boosters such as amine oxides (see for example U.S. Pat. No. 4,133,779) and/or skin feel modifiers of surfactant, emollient and/or enzymatic types including proteases; and/or antimicrobial agents; more comprehensive patent listings are given in Surfactant Science Series, Vol. 67, pages 240–248.

Heavy Duty Liquid Detergents (HDL): these compositions include both the so-called "structured" or multi-phase (see for example U.S. Pat. No. 4,452,717; U.S. Pat. No. 4,526,709; U.S. Pat. No. 4,530,780; U.S. Pat. No. 4,618,446; U.S. Pat. No. 4,793,943; U.S. Pat. No. 4,659,497; U.S. Pat. No. 4,871,467; U.S. Pat. No. 4,891,147; U.S. Pat. No. 5,006,273; U.S. Pat. No. 5,021,195; U.S. Pat. No. 5,147,576; U.S. Pat. No. 5,160,655) and "non-structured" or isotropic liquid types and can in general be aqueous or nonaqueous (see, for example EP 738,778 A; WO 97/00937 A; WO 97/00936 A; EP 752,466 A; DE 19623623 A; WO 96/10073 A; WO 96/10072 A; U.S. Pat. No. 4,647,393; U.S. Pat. No. 4,648,983; U.S. Pat. No. 4,655,954; U.S. Pat. No. 4,661,280; EP 225,654; U.S. Pat. No. 4,690,771; U.S. Pat. No. 4,744,916; U.S. Pat. No. 4,753,750; U.S. Pat. No. 4,950,424; U.S. Pat. No. 5,004,556; U.S. Pat. No. 5,102,574; WO 94/23009; and can be with bleach (see for example U.S. Pat. No. 4,470,919; U.S. Pat. No. 5,250,212; EP 564,250; U.S. Pat. No. 5,264,143; U.S. Pat. No. 5,275,753; U.S. Pat. No. 5,288,746; WO 94/11483; EP 598,170; EP 598,973; EP 619,368; U.S. Pat. No. 5,431,848; U.S. Pat. No. 5,445,756) and/or enzymes (see for example U.S. Pat. No. 3,944,470; U.S. Pat. No. 4,111,855; U.S. Pat. No. 4,261,868; U.S. Pat. No. 4,287,082; U.S. Pat. No. 4,305,837; U.S. Pat. No. 4,404,115; U.S. Pat. No. 4,462,922; U.S. Pat. No. 4,529,5225; U.S. Pat. No. 4,537,706; U.S. Pat. No. 4,537,707; U.S. Pat. No. 4,670,179; U.S. Pat. No. 4,842,758; U.S. Pat. No. 4,900,475; U.S. Pat. No. 4,908,150; U.S. Pat. No. 5,082,585; U.S. Pat. No. 5,156,773; WO 92/19709; EP 583,534; EP 583,535; EP 583,536; WO 94/04542; U.S. Pat. No. 5,269,960; EP 633,311; U.S. Pat. No. 5,422,030; U.S. Pat. No. 5,431,842; U.S. Pat. No. 5,442,100) or without bleach and/or enzymes. Other patents relating to heavy-duty liquid detergents are tabulated or listed in Surfactant Science Series, Vol. 67, pages 309–324.

Heavy Duty Granular Detergents (HDG): these compositions include both the so-called "compact" or agglomerated or otherwise non-spray-dried, as well as the so-called "fluffy" or spray-dried types. Included are both phosphated and nonphosphated types. Such detergents can include the more common anionic-surfactant based types or can be the so-called "high-nonionic surfactant" types in which commonly the nonionic surfactant is held in or on an absorbent such as zeolites or other porous inorganic salts. Manufacture of HDG's is, for example, disclosed in EP 753,571 A; WO 96/38531 A; U.S. Pat. No. 5,576,285; U.S. Pat. No. 5,573,697; WO 96/34082 A; U.S. Pat. No. 5,569,645; EP 739,977 A; U.S. Pat. No. 5,565,422; EP 737,739 A; WO 96/27655 A; U.S. Pat. No. 5,554,587; WO 96/25482 A; WO 96/23048 A; WO 96/22352 A; EP 709,449 A; WO 96/09370 A; U.S. Pat. No. 5,496,487; U.S. Pat. No. 5,489,392 and EP 694,608 A.

"Softergents" (STW): these compositions include the various granular or liquid (see for example EP 753,569 A; U.S. Pat. No. 4,140,641; U.S. Pat. No. 4,639,321; U.S. Pat. No. 4,751,008; EP 315,126; U.S. Pat. No. 4,844,821; U.S. Pat. No. 4,844,824; U.S. Pat. No. 4,873,001; U.S. Pat. No. 4,911,852; U.S. Pat. No. 5,017,296; EP 422,787) softening-through-the wash types of product and in general can have organic (e.g., quaternary) or inorganic (e.g., clay) softeners.

Hard Surface Cleaners (HSC): these compositions include all-purpose cleaners such as cream cleansers and liquid all-purpose cleaners; spray all-purpose cleaners including glass and tile cleaners and bleach spray cleaners; and bathroom cleaners including mildew-removing, bleach-containing, antimicrobial, acidic, neutral and basic types. See, for example EP 743,280 A; EP 743,279 A. Acidic cleaners include those of WO 96/34938 A.

Bar Soaps and/or Laundry Bars (BS&HW): these compositions include personal cleansing bars as well as so-called laundry bars (see, for example WO 96/35772 A); including both the syndet and soap-based types and types with softener (see U.S. Pat. No. 5,500,137 or WO 96/01889 A); such compositions can include those made by common soap-making techniques such as plodding and/or more unconventional techniques such as casting, absorption of surfactant into a porous support, or the like. Other bar soaps (see for example BR 9502668; WO 96/04361 A; WO 96/04360 A; U.S. Pat. No. 5,540,852) are also included. Other handwash detergents include those such as are described in GB 2,292, 155 A and WO 96/01306 A.

Shampoos and Conditioners (S&C): (see, for example WO 96/37594 A; WO 96/17917 A; WO 96/17590 A; WO 96/17591 A). Such compositions in general include both simple shampoos and the so-called "two-in-one" or "with conditioner" types.

Liquid Soaps (LS): these compositions include both the so-called "antibacterial" and conventional types, as well as those with or without skin conditioners and include types suitable for use in pump dispensers, and by other means such as wall-held devices used institutionally.

Special Purpose Cleaners (SPC): including home dry cleaning systems (see for example WO 96/30583 A; WO 96/30472 A; WO 96/30471 A; U.S. Pat. No. 5,547,476; WO 96/37652 A); bleach pretreatment products for laundry (see EP 751,210 A); fabric care pretreatment products (see for example EP 752,469 A); liquid fine fabric detergent types, especially the high-foaming variety; rinse-aids for dishwashing; liquid bleaches including both chlorine type and oxygen bleach type, and disinfecting agents, mouthwashes, denture cleaners (see, for example WO 96/19563 A; WO 96/19562 A), car or carpet cleaners or shampoos (see, for example EP 751,213 A; WO 96/15308 A), hair rinses, shower gels, foam baths and personal care cleaners (see, for example WO 96/37595 A; WO 96/37592 A; WO 96/37591 A; WO 96/37589 A; WO 96/37588 A; GB 2,297,975 A; GB 2,297,762 A; GB 2,297,761 A; WO 96/17916 A; WO 96/12468 A) and metal cleaners; as well as cleaning auxiliaries such as bleach additives and "stain-stick" or other pre-treat types including special foam type cleaners (see, for example EP 753,560 A; EP 753,559 A; EP 753,558 A; EP 753,557 A; EP 753,556 A) and anti-sunfade treatments (see WO 96/03486 A; WO 96/03481 A; WO 96/03369 A) are also encompassed.

Detergents with enduring perfume (see for example U.S. Pat. No. 5,500,154; WO 96/02490) are increasingly popular.

Process Integration

The present process can be integrated with current LAB manufacturing processes in any convenient manner. For example, conventional erected plant can be switched to produce the modified alkylbenzenes in their entirety. Alternately, depending on volumes desired or feedstocks available, for example as effluents from the LAB process or based on proximity of feedstock sources from the petrochemical industry, plant for the manufacture of the instant modified alkylbenzenes may be erected as an add-on or complement to an existing LAB facility, or as a stand-alone. Both batch and continuous operation of the present process are envisaged.

In one add-on mode, the present invention encompasses steps of making vinylidene olefin and from the vinylidene olefin, modified alkylbenzene or alkyltoluene using the steps described in detail hereinabove. The modified alkylbenzene or alkyltoluene is blended at a ratio of from about 1:100 to 100:1, more typically from about 1:10 to about 10:1, for example about 1:5, into a conventional linear alkylbenzene, for example a C11.8 average alkylbenzene or any alkylbenzene produced by the DETAL® process. The blend is then sulfonated, neutralized and incorporated into consumer cleaning product compositions.

The present invention should not be considered limited by the specifics of its illustration in the specification including the examples given for illustration hereinafter. Most generally, the present invention should be taken to encompass any consumer cleaning composition comprising any surfactant product of any type wherein the hydrophobe of the surfactant has been modified by an approach using the essential teachings of the instant process. The present teachings, especially with respect to the delinearization approach, are believed to be reapplicable, for example, to the manufacture of modified alkyl sulfates and other surfactants.

EXAMPLE 1

Modified Alkylbenzenesulfonate Prepared via Branched Hydrocarbon-containing Feeds Sourced from Jet/diesel; with Separation over SAPO-11; Dehydrogenation; Alkylation Over H-mordenite; Sulfonation Using Sulfur Trioxide/air; and Neutralization A suitable feed is obtained in the form of a jet/diesel distillation cut from kerosene. This feed contains paraffinic branched and linear hydrocarbons, wherein the linear hydrocarbons are of suitable chainlength for LAB manufacture and wherein the branched hydrocarbons include at least about 10% of methyl branched paraffins; along with cyclic hydrocarbons, aromatics and other impurities. This stream is passed continuously to two adsorptive separation units, connected as shown in FIG. 8 and FIG. 1 wherein unit ACI of detail FIG. 8 is loaded with 5 Angstrom Ca zeolite as used in conventional linear alkylbenzene manufacture and unit AC2 of detail FIG. 8 is loaded with the silicoaluminophosphate SAPO-11. The units AC1 and AC2 along with the associated rotary valve devices, raffinate columns and effluent columns (RC and EC) and condensers (shown as unlabelled horizontal tanks in FIG. 8.) and other means shown, though connected in unique manner, are of construction generally in accordance with units licensable and commercially available through UOP Corp. (MOLEX® units). The raffinate from the Ca zeolite adsorptive unit AC1 is rejected and the adsorbate (effluent) is passed continuously to the second adsorptive separation unit AC2 containing the SAPO-11. The branched-enriched stream taken from unit AC2 as adsorbate or extract is passed to a standard commercial LAB process dehydrogenation unit provided by UOP Corp. (PACOL process) charged with a standard LAB dehydrogenation catalyst (DeH 5 or DeH 7 or similar) proprietary to UOP Corp. After dehydrogenation under conventional LAB-making process conditions, the hydrocarbons are passed continuously to an alkylation unit which is otherwise conventional but is charged with H-mordenite (ZEOCAT FM 8/25 H) where alkylation proceeds continuously at a temperature of about 200 deg. C with discharge on reaching a completion of at least about 90%, that is, a conversion of the input hydrocarbon of at least about 90%. This produces a modified alkylbenzene. A recycle of paraffins is obtained by distillation at the back-end of the alkylation unit and the recycle is passed back to the dehydrogenator. The process to this point includes the steps and streams of FIG. 1. The modified alkylbenzene can be further purified by additional conventional distillation (such distillative steps are not shown in FIG. 1). The distilled modified alkylbenzene mixture is sulfonated batchwise or continuously, at a remote facility if desired, using sulfur trioxide as sulfonating agent. Details of sulfonation using a suitable air/sulfur trioxide mixture are provided in U.S. Pat. No. 3,427,342, Chemithon. The modified alkylbenzenesulfonic acid product of the preceding step is neutralized with sodium hydroxide to give modified alkylbenzene sulfonate, sodium salt mixture.

EXAMPLE 2

Modified Alkylbenzenesulfonate Prepared via Hydrocaron Feed Sourced from Molex Effluent, Separation Over SAPO-11, Dehydrogenation Using Standard UOP Method, Alkylation Over H-mordenite, Sulfonation Using Sulfur Trioxide/air, and Neutralization A suitable feedstock is obtained in the form of effluent or raffinate from an LAB plant, specifically the MOLEX process unit of such a plant. This raffinate contains a high proportion of branched paraffinic hydrocarbons along with undesirable cyclic hydrocarbons, aromatics and other impurities. This raffinate is passed continuously to an adsorptive separation unit constructed conventionally, e.g., after the manner of a MOLEX® unit, but having a charge of SAPO-11. This unit operates under conditions generally similar to the MOLEX® unit as used in linear alkylbenzene manufacture and resembles the unit AC2 described in Example 1. The raffinate or effluent from the SAPO-11 adsorptive unit is rejected and the adsorbate or extract now meeting the invention definition of a branched-enriched stream is passed continuously to a standard commercial LAB process dehydrogenation unit provided by UOP Corp. (PACOL® process) charged with a standard LAB dehydrogenation catalyst (e.g., DeH 7) proprietary to UOP Corp. After dehydrogenation under conventional LAB-making process conditions, the hydrocarbons are passed continuously to an alkylation unit which is otherwise conventional but is charged with H-mordenite (ZEOCAT FM 8/25 H) where alkylation proceeds continuously at a temperature of about 200 deg. C with discharge on reaching an alkylating agent conversion of at least about 90%. The modified alkylbenzene mixture is purified by conventional distillation and branched paraffins are recycled to the dehydrogenation unit. Steps in the process to this point follow FIG. 4.

The distilled modified alkylbenzene mixture produced in process to this point is sulfonated batchwise or continuously, at a remote facility if desired, using sulfur trioxide as sulfonating agent. Details of sulfonation using a suitable air/sulfur trioxide mixture are provided in U.S. Pat. No. 3,427,342, Chemithon. The modified alkylbenzenesulfonic acid product of the preceding step is neutralized with sodium hydroxide to give modified alkylbenzene sulfonate, sodium salt mixture.

EXAMPLE 3

Modified Alkylbenzenesulfonate Prepared via Hydrocarbon Feed Sourced from Molex Effluent, Separation Over Pyrolyzed Poly(vinylidene Chloride), Dehydrogenation Using Standard UOP Method, Alkylation Over H-ZSM-12, Sulfonation Using Sulfur Trioxide/air and Neutralization A suitable feedstock is obtained in the form of effluent or raffinate from an LAB plant, specifically the MOLEX® process unit of such a plant. This raffinate contains branched paraffinic hydrocarbons along with cyclic hydrocarbons, aromatics and other undesired impurities. This raffinate is passed continuously to an adsorptive separation unit of conventional construction, e.g., MOLEX® type, not conventionally being incorporated in LAB plant design and hereinafter termed the "SARAN unit" having a charge of pyrolyzed poly(vinylidene chloride), sieve diameter >5 Angstrom, manufactured according to Netherlands Application NL 7111508 published Oct. 25, 1971. The "SARAN unit" operates under conditions similar to the MOLEX® unit. The raffinate from the "SARAN unit" is rejected and the adsorbate is passed continuously to a standard commercial LAB process dehydrogenation unit provided by UOP Corp. (PACOL® process) charged with a standard LAB dehydrogenation catalyst such as DeH 7 proprietary to UOP Corp. After dehydrogenation under conventional LAB-making process conditions, the hydrocarbons are passed continuously to an alkylation unit which is otherwise conventional but is charged with H-ZSM 12 where alkylation proceeds continuously at a temperature of about 200 deg. C with discharge on reaching a conversion of the input hydrocarbon of at least about 90%. The modified alkylbenzene mixture produced in the preceding step is distilled and sulfonated batchwise or continuously using sulfur trioxide as sulfonating agent. Details of sulfonation using a suitable air/sulfur trioxide mixture are provided in U.S. Pat. No. 3,427,342, Chemithon. The modified alkylbenzenesulfonic acid product of the preceding step is neutralized with sodium hydroxide to give modified alkylbenzene sulfonate, sodium salt mixture.

EXAMPLE 4

Modified Alkylbenzenesulfonate Prepared via Hydrocarbon Feed from Urea Clathration, Separation Over SAPO-11, Dehydrogenation Using Pt Catalyst, Alkylation Over Zeolite Beta (acid form), Sulfonation Using Sulfur Trioxide/air and Neutralization A suitable feedstock is obtained from kerosene by urea clathration which is used to remove a fraction rich in the more commercially valuable linear hydrocarbons. See U.S. Pat. No. 3,506,569. The low-grade branched effluent from the urea clathration stage is a suitable hydrocarbon feed for the present process. It is stripped of any activator solvent such as methanol, if present, and is passed continuously to an adsorptive separation unit constructed in any conventional manner, for example after the fashion of MOLEX® process units, but differently charged, having a charge of SAPO-11. The SAPO-11 unit operates under conditions similar to a standard MOLEX® process unit. The raffinate from the SAPO-11 unit is rejected and the adsorbate is passed continuously to a standard commercial LAB process dehydrogenation unit provided by UOP Corp. (PACOL® process) charged with a nonproprietary Platinum dehydrogenation catalyst. After dehydrogenation under conventional LAB-making process conditions, the hydrocarbons are passed continuously to an alkylation unit which is otherwise conventional but is charged with H-ZSM 12 where alkylation proceeds continuously at a temperature of about 200 deg. C with discharge on reaching a conversion of the input hydrocarbon of at least about 90%. The modified alkylbenzene mixture produced in the preceding step is sulfonated batchwise or continuously using sulfur trioxide as sulfonating agent. Details of sulfonation using a suitable air/sulfur trioxide mixture are provided in U.S. Pat. No. 3,427,342, Chemithon. The modified alkylbenzenesulfonic acid product of the preceding step is neutralized with sodium hydroxide to give modified alkylbenzene sulfonate, sodium salt mixture.

EXAMPLE 5

Modified Alkylbenzenesulfonate Prepared via Hydrocarbon Feed from Kerosene Cut from a High Paraffinic Petroleum Source, Separation Over Grafted Nonacidic Zeolite, Dehydrogenation Using DeH 9 Catalyst, Alkylation Over H-mordenite, Sulfonation Using Chlorosulfonic Acid, and Neutralization A jet/kerosene cut is taken from a low-viscosity crude, e.g., Brent light. This is passed continuously to an adsorptive separation unit constructed in any conventional manner, for example after the fashion of MOLEX® process units, but differently charged, having a charge of grafted zeolite prepared in accordance with U.S. Pat. No. 5,326,928. The unit operates under conditions similar to a conventionally charged MOLEX® unit. The raffinate from this unit is rejected and the adsorbate is passed continuously to a standard commercial LAB process dehydrogenation unit provided by UOP Corp. (PACOL® process) charged with a standard LAB dehydrogenation catalyst DeH 9 proprietary to UOP Corp. After dehydrogenation under conventional LAB-making process conditions, the hydrocarbons are passed continuously to an alkylation unit which is otherwise conventional but is charged with H-mordenite (ZEOCAT FM 8/25 H) where alkylation proceeds continuously at a temperature of about 200 deg. C with discharge on reaching a conversion of the input hydrocarbon of at least about 90%. The modified alkylbenzene mixture produced in the preceding step is sulfonated batchwise or continuously using sulfur trioxide as sulfonating agent. Details of sulfonation using a suitable air/sulfur trioxide mixture are provided in U.S. Pat. No. 3,427,342, Chemithon. The modified alkylbenzenesulfonic acid product of the preceding step is neutralized with sodium hydroxide to give modified alkylbenzene sulfonate, sodium salt mixture.

EXAMPLE 6

Cleaning Product Composition

10% by weight of modified alkylbenzenesulfonate sodium salt product of any of the foregoing exemplified processes is combined with 90% by weight of an agglomerated compact laundry detergent granule.

EXAMPLE 7

Cleaning Product Compositions

In this Example, the following abbreviation is used for a modified alkylbenzene sulfonate, sodium salt form or potassium salt form, prepared according to any of the preceding process examples: MAS The following abbreviations are used for cleaning product adjunct materials:

| | |
|---|---|
| Amylase | Amylolytic enzyme, 60KNU/g, NOVO, Termamyl ® 60T |
| APA | C8–C10 amido propyl dimethyl amine |
| Bicarbonate | Sodium bicarbonate, anhydrous, 400 μm–1200 μm |
| Borax | Na tetraborate decahydrate |
| Brightener 1 | Disodium 4,4'-bis(2-sulphostyryl)biphenyl |
| Brightener 2 | Disodium 4,4'-bis(4-anilino-6-morpholino-1.3.5-triazin-2-yl)amino) stilbene-2:2'-disulfonate |
| C45AS | $C_{14}$–$C_{15}$ linear alkyl sulfate, Na salt |
| $CaCl_2$ | Calcium chloride |
| Carbonate | $Na_2CO_3$ anhydrous, 200 μm–900 μm |
| Cellulase | Cellulolytic enzyme, 1000 CEVU/g, NOVO, Carezyme ® |
| Citrate | Trisodium citrate dihydrate, 86.4%, 425 μm–850 μm |
| Citric Acid | Citric Acid, Anhydrous |
| CMC | Sodium carboxymethyl cellulose |
| CxyAS | $C_{1x}$–$C_{1y}$ alkyl sulfate, Na salt or other salt if specified |
| CxyEz | $C_{1x-1y}$ branched primary alcohol ethoxylate (average z moles of ethylene oxide) |
| CxyEzS | $C_{1x}$–$C_{1y}$ alkyl ethoxylate sulfate, Na salt (average z moles of ethylene oxide; other salt if specified) |
| CxyFA | $C_{1x}$–$C_{1y}$ fatty acid |

-continued

| | |
|---|---|
| Diamine | Alkyl diamine, e.g., 1,3 propanediamine, Dytek EP, Dytek A, (Dupont) |
| Dimethicone | 40 (gum)/60 (fluid) wt. Blend of SE-76 dimethicone gum (G.E Silicones Div.)/dimethicone fluid of viscosity 350 cS. |
| DTPA | Diethylene triamine pentaacetic acid |
| DTPMP | Diethylene triamine penta (methylene phosphonate), Monsanto (Dequest 2060) |
| Endolase | Endoglucanase, activity 3000 CEVU/g, NOVO |
| EtOH | Ethanol |
| Fatty Acid (C12/14) | C12–C14 fatty acid |
| Fatty Acid (RPS) | Rapeseed fatty acid |
| Fatty Acid (TPK) | Topped palm kernel fatty acid |
| HEDP | 1,1-hydroxyethane diphosphonic acid |
| Isofol 16 | C16 (average) Guerbet alcohols (Condea) |
| LAS | Linear Alkylbenzene Sulfonate (C11.8, Na or K salt) |
| Lipase | Lipolytic enzyme, 100kLU/g, NOVO, Lipolase ® |
| LMFAA | C12–14 alkyl N-methyl glucamide |
| LMFAA | C12–14 alkyl N-methyl glucamide |
| MA/AA | Copolymer 1:4 maleic/acrylic acid, Na salt, avg. mw. 70,000. |
| $MBAE_x$ | Mid-chain branched primary alkyl ethoxylate (average total carbons = x; average EO = 8) |
| $MBAE_xS_z$ | Mid-chain branched primary alkyl ethoxylate sulfate, Na salt (average total carbons = z; average EO = x) |
| $MBAS_x$ | Mid-chain branched primary alkyl sulfate, Na salt (average total carbons = x) |
| MEA | Monoethanolamine |
| MES | Alkyl methyl ester sulfonate, Na salt |
| $MgCl_2$ | Magnesium chloride |
| MnCAT | Macrocyclic Manganese Bleach Catalyst as in EP 544,440 A or, preferably, use [Mn (Bcyclam)$Cl_2$] wherein Bcyclam = 5,12-dimethyl-1,5,8,12-tetraaza-bicyclo[6.6.2] hexadecane or a comparable bridged tetra-aza macrocycle |
| NaDCC | Sodium dichloroisocyanurate |
| NaOH | Sodium hydroxide |
| NaPS | Paraffin sulfonate, Na salt |
| NaSKS-6 | Crystalline layered silicate of formula δ-$Na_2Si_2O_5$ |
| NaTS | Sodium toluene sulfonate |
| NOBS | Nonanoyloxybenzene sulfonate, sodium salt |
| LOBS | C12 oxybenzenesulfonate, sodium salt |
| PAA | Polyacrylic Acid (mw = 4500) |
| PAE | Ethoxylated tetraethylene pentamine |
| PAEC | Methyl quaternized ethoxylated dihexylene triamine |
| PB1 | Anhydrous sodium perborate bleach of nominal formula $NaBO_2.H_2O_2$ |
| PEG | Polyethylene glycol (mw = 4600) |
| Percarbonate | Sodium Percarbonate of nominal formula $2Na_2CO_3.3H_2O_2$ |
| PG | Propanediol |
| Photobleach | Sulfonated Zinc Phthalocyanine encapsulated in dextrin soluble polymer |
| PIE | Ethoxylated polyethyleneimine |
| Protease | Proteolytic enzyme, 4KNPU/g, NOVO, Savinase ® |
| QAS | $R_2.N^+(CH_3)_x((C_2H_4O)yH)z$ with $R_2$ = $C_8$–$C_{18}$ x + z = 3, x = 0 to 3, z = 0 to 3, y = 1 to 15. |
| SAS | Secondary alkyl sulfate, Na salt |
| Silicate | Sodium Silicate, amorphous ($SiO_2$:$Na_2O$; 2.0 ratio) |
| Silicone antifoam | Polydimethylsiloxane foam controller + siloxane-oxyalkylene copolymer as dispersing agent; ratio of foam controller dispersing agent = 10:1 to 100:1. |
| SRP 1 | Sulfobenzoyl end capped esters with oxyethylene oxy and terephthaloyl backbone |
| SRP 2 | Sulfonated ethoxylated terephthalate polymer |
| SRP 3 | Methyl capped ethoxylated terephthalate polymer |
| STPP | Sodium tripolyphosphate, anhydrous |
| Sulfate | Sodium sulfate, anhydrous |
| TAED | Tetraacetylethylenediamine |
| TFA | C16–18 alkyl N-methyl glucamide |
| Zeolite A | Hydrated Sodium Aluminosilicate, $Na_{12}(AlO_2SiO_2)_{12}.27H_2O$; 0.1–10 μm |
| Zeolite MAP | Zeolite (Maximum aluminum P) detergent grade (Crosfield) |

The example is illustrative of the present invention, but is not meant to limit or otherwise define its scope. All parts, percentages and ratios used are expressed as percent weight unless otherwise noted. The following laundry detergent compositions A to F are prepared in accordance with the invention:

|  | A | B | C | D | E | F |
|---|---|---|---|---|---|---|
| MAS | 22 | 16.5 | 11 | 1–5.5 | 10–25 | 5–35 |
| Any Combination of | 0 | 1–5.5 | 11 | 16.5 | 0–5 | 0–10 |
| C45 AS |  |  |  |  |  |  |
| C45E1S |  |  |  |  |  |  |
| LAS |  |  |  |  |  |  |
| C16 SAS |  |  |  |  |  |  |
| C14–17 NaPS |  |  |  |  |  |  |
| C14–18 MES |  |  |  |  |  |  |
| MBAS16.5 |  |  |  |  |  |  |
| MBAE2S15.5 |  |  |  |  |  |  |
| QAS | 0–2 | 0–2 | 0–2 | 0–2 | 0–4 | 0 |
| C23E6.5 or C45E7 | 1.5 | 1.5 | 1.5 | 1.5 | 0–4 | 0–4 |
| Zeolite A | 27.8 | 0 | 27.8 | 27.8 | 20–30 | 0 |
| Zeolite MAP | 0 | 27.8 | 0 | 0 | 0 | 0 |
| Na tripolyphosphate | 0 | 0 | 0 | 0 | 0 | 5–40 |
| PAA | 2.3 | 2.3 | 2.3 | 2.3 | 0–5 | 0–5 |
| Carbonate | 27.3 | 27.3 | 27.3 | 27.3 | 20–30 | 0–30 |
| Silicate | 0.6 | 0.6 | 0.6 | 0.6 | 0–2 | 0–6 |
| PB1 | 1.0 | 1.0 | 0–10 | 0–10 | 0–10 | 0–20 |
| NOBS | 0–1 | 0–1 | 0–1 | 0.1 | 0.5–3 | 0–5 |
| LOBS | 0 | 0 | 0–3 | 0 | 0 | 0 |
| TAED | 0 | 0 | 0 | 2 | 0 | 0–5 |
| MnCAT | 0 | 0 | 0 | 0 | 2 ppm | 0–1 |
| Protease | 0–0.5 | 0–0.5 | 0–0.5 | 0–0.5 | 0–0.5 | 0–1 |
| Cellulase | 0–0.3 | 0–0.3 | 0–0.3 | 0–0.3 | 0–0.5 | 0–1 |
| Amylase | 0–0.5 | 0–0.5 | 0–0.5 | 0–0.5 | 0–1 | 0–1 |
| SRP 1 or SRP 2 | 0.4 | 0.4 | 0.4 | 0.4 | 0–1 | 0–5 |
| Brightener 1 or 2 | 0.2 | 0.2 | 0.2 | 0.2 | 0–0.3 | 0–5 |
| PEG | 1.6 | 1.6 | 1.6 | 1.6 | 0–2 | 0–3 |
| Silicone Antifoam | 0.42 | 0.42 | 0.42 | 0.42 | 0–0.5 | 0–1 |
| Sulfate, Water, Minors | to 100% | to 100% | to 100% | to 100% | to 100% | to 100% |
| Density (g/L) | 400–700 | 600–700 | 600–700 | 600–700 | 600–700 | 450–700 |

EXAMPLE 8

Cleaning Product Compositions

The following liquid laundry detergent compositions A to E are prepared in accord with the invention. Abbreviations are as used in the preceding Examples.

|  | A | B | C | D | E |
|---|---|---|---|---|---|
| MAS | 1–7 | 7–12 | 12–17 | 17–22 | 1–35 |
| Any combination of | 15–21 | 10–15 | 5–10 | 0–5 | 0–25 |
| C25 AExS*Na (x = 1.8 – 2.5) |  |  |  |  |  |
| MBAE1.8S15.5 |  |  |  |  |  |
| MBAS15.5 |  |  |  |  |  |
| C25 AS (linear to high 2-alkyl) |  |  |  |  |  |
| C14–17 NaPS |  |  |  |  |  |
| C12–16 SAS |  |  |  |  |  |
| C18 1,4 disulfate |  |  |  |  |  |
| LAS |  |  |  |  |  |
| C12–16 MES |  |  |  |  |  |
| LMFAA | 0–3.5 | 0–3.5 | 0–3.5 | 0–3.5 | 0–8 |
| C23E9 or C23E6.5 | 0–2 | 0–2 | 0–2 | 0–2 | 0–8 |
| APA | 0–0.5 | 0–0.5 | 0–0.5 | 0–0.5 | 0–2 |
| Citric Acid | 5 | 5 | 5 | 5 | 0–8 |

-continued

|  | A | B | C | D | E |
|---|---|---|---|---|---|
| Fatty Acid (TPK or C12/14) | 2 | 2 | 2 | 2 | 0–14 |
| EtOH | 4 | 4 | 4 | 4 | 0–8 |
| PG | 6 | 6 | 6 | 6 | 0–10 |
| MEA | 1 | 1 | 1 | 1 | 0–3 |
| NaOH | 3 | 3 | 3 | 3 | 0–7 |
| Na TS | 2.3 | 2.3 | 2.3 | 2.3 | 0–4 |
| Na formate | 0.1 | 0.1 | 0.1 | 0.1 | 0–1 |
| Borax | 2.5 | 2.5 | 2.5 | 2.5 | 0–5 |
| Protease | 0.9 | 0.9 | 0.9 | 0.9 | 0–1.3 |
| Lipase | 0.06 | 0.06 | 0.06 | 0.06 | 0–0.3 |
| Amylase | 0.15 | 0.15 | 0.15 | 0.15 | 0–0.4 |
| Cellulase | 0.05 | 0.05 | 0.05 | 0.05 | 0–0.2 |
| PAE | 0–0.6 | 0–0.6 | 0–0.6 | 0–0.6 | 0–2.5 |
| PIE | 1.2 | 1.2 | 1.2 | 1.2 | 0–2.5 |
| PAEC | 0–0.4 | 0–0.4 | 0–0.4 | 0–0.4 | 0–2 |
| SRP 2 | 0.2 | 0.2 | 0.2 | 0.2 | 0–0.5 |
| Brightener 1 or 2 | 0.15 | 0.15 | 0.15 | 0.15 | 0–0.5 |
| Silicone antifoam | 0.12 | 0.12 | 0.12 | 0.12 | 0–0.3 |
| Fumed Silica | 0.0015 | 0.0015 | 0.0015 | 0.0015 | 0–0.003 |
| Perfume | 0.3 | 0.3 | 0.3 | 0.3 | 0–0.6 |
| Dye | 0.0013 | 0.0013 | 0.0013 | 0.0013 | 0–0.003 |
| Moisture/minors | Balance | Balance | Balance | Balance | Balance |
| Product pH (10% in DI water) | 7.7 | 7.7 | 7.7 | 7.7 | 6–9.5 |

What is claimed is:

1. A process for preparing a modified alkylaryl comprising the steps of:
   (a)(1) providing a hydrocarbon feed selected from the group consisting of olefinic feeds, paraffinic feeds and mixtures thereof, said hydrocarbon feed comprising branched aliphatic hydrocarbons having from about 8 to about 20 carbon atoms;
   (a)(2) separating said hydrocarbon feed into:
      i. at least one branched-enriched stream comprising an increased proportion of branched acyclic hydrocarbons relative to said hydrocarbon feed; and
      ii. optionally, one or more of the following streams:
         a. a linear-enriched stream comprising an increased proportion of linear aliphatic hydrocarbons relative to said hydrocarbon feed; and
         b. a reject stream comprising cyclic and/or aromatic hydrocarbons;
      wherein the step of separating comprises a step selected from the group consisting of: adsorptive separation using porous media; clathration using a clathrating compound selected from urea, thiourea, alternative clathrating amides and mixtures thereof; and mixtures thereof;
      wherein said step of separating comprises a simulated moving bed adsorptive means comprising: at least one bed holding said porous media and/or clathrating compound; and a device for simulating motion of said porous media and/or clathrating compound countercurrent to a hydrocarbon stream in said at least one bed;
   (b) when said hydrocarbon feed comprises less than about 5% of olefins, at least partially dehydrogenating the said at least one branched-enriched stream; and
   (c) reacting said at least one branched-enriched stream produced from step (a)(2) and/or said dehydrogenated branched-enriched stream from step (b), with an aromatic hydrocarbon selected from the group consisting of: benzene, toluene and mixtures thereof, in the presence of an alkylation catalyst to produce a modified alkylaryl.

2. The process according to claim 1 wherein said simulated moving bed adsorptive means comprises two or more beds, wherein at least two of said two or more beds comprise different porous media relative to each.

3. The process according to claim 2 wherein said different porous media differ from one another by an increased capacity to retain methyl-branched acyclic aliphatic hydrocarbons.

4. The process according to claim 2 wherein said at least two of said two or more beds comprise different devices.

5. The process according to claim 4 wherein said devices comprise at least eight ports for achieving simulated movement of said porous media in said at least two of said two or more beds.

6. The process according to claim 3 wherein said two or more beds are connected such that a proportion of methyl branched acyclic aliphatic hydrocarbons in said at least one branched-enriched stream from step (a) is at least partially increased and/or that a proportion of linear acyclic aliphatic hydrocarbons in said at least one branched-enriched stream from step (a) is at least partially decreased.

7. The process according to claim 1 wherein step (c) comprises an internal isomer selectivity of from 0 to about 40.

8. The process according to claim 2 wherein at least one of said two or more beds comprises a porous media capable of producing linear alkylaryls.

9. The process according to claim 1 wherein said simulated moving bed absorptive means further comprises one or more additional said devices.

10. The process according to claim 1 wherein said at least one bed comprises at least eight sub-beds, wherein said at least eight sub-beds are arranged in a vertically positioned array.

11. The process according to claim 1 wherein step (a)(2) comprises separating said hydrocarbon feed into two or more distinct streams comprising said at least one branched-enriched stream and one or more of the following: said linear-enriched stream and said reject stream, by said simulated moving bed absorptive means.

12. The process according to claim 11 wherein said step of separating said hydrocarbon feed into said distinct streams occurs simultaneously.

13. The process according to claim 11 wherein said step of separating said hydrocarbon feed into said distinct streams occurs sequentially.

14. The process according to claim 13 wherein said reject stream is separated from said hydrocarbon feed first.

15. The process according to claim 13 wherein said linear-enriched stream is separated from said hydrocarbon feed first.

16. The process according to claim 13 wherein said branched-enriched stream is separated from said hydrocarbon feed first.

17. The process according to claim 1 wherein said reject stream, when present, comprises undesired branched hydrocarbons selected from the group consisting of: gem-dimethyl branched hydrocarbons, ethyl branched hydrocarbons, and higher than ethyl branched hydrocarbons and mixtures thereof.

18. The process according to claim 17 wherein said at least one branched-enriched stream comprises a reduced proportion of said gem-dimethyl branched hydrocarbons, ethyl branched hydrocarbons, and higher than ethyl branched hydrocarbons relative to said hydrocarbon feed.

19. The process according to claim 1 wherein said porous media comprises zeolites.

20. The process according to claim 19 wherein said zeolites are selected from the group consisting of smaller-pore zeolites, larger-pore zeolites and mixtures thereof.

21. The process according to claim 1 wherein said porous media comprises porous media having a minimum pore size larger than the pore size required for selective adsorption of linear acyclic hydrocarbons, but not exceeding about 20 Angstroms.

22. The process according to claim 1 wherein said linear-enriched stream is separated from said hydrocarbon feed in step (a)(2) by contacting said hydrocarbon feed with at least one bed comprising smaller-pore zeolite porous media.

23. The process according to claim 1 wherein said reject steam is separated from said hydrocarbon feed in step (a)(2) by contacting said hydrocarbon feed with at least one bed comprising larger-pore zeolite porous media.

24. The process according to claim 7 wherein step (c) comprises an internal isomer selectivity of from 0 to about 20.

25. The process according to claim 7 wherein said alkylation catalyst selected from the group consisting of: mordenites, zeolite betas and mixtures thereof.

26. The process according to claim 7 wherein said alkylation catalyst is at least partially dealuminized.

27. The process according to claim 1 wherein said hydrocarbon feed comprises at least about 10% methyl-branched paraffins having a molecular weight of from at least about 128 to no more than about 282.

28. The process according to claim 27 wherein said hydrocarbon feed comprises at least about 20% methyl-branched paraffins having a molecular weight of from at least about 128 to no more than about 226.

29. The process according to claim 1 wherein said hydrocarbon feed comprises at least about 10% methyl-branched olefins having a molecular weight of from at least about 128 to no more than about 282.

30. The process according to claim 29 wherein said hydrocarbon feed comprises at least about 50% methyl-branched olefins having a molecular weight of from at least about 128 to no more than about 226.

31. The process according to claim 1 wherein said hydrocarbon feed comprises an adsorptive separation raffinate and/or effluent derived from a linear alkylaryl manufacturing process.

32. The process according to claim 1 wherein said separation step (a)(2) comprises contacting the hydrocarbon feed and/or said at least one branched-enriched stream and/or said linear-enriched stream and/or said reject stream with an organometallic-grafted mordenite.

33. The process according to claim 32 wherein said organometallic-grafted mordenite comprises a tin-grafted mordenite.

* * * * *

UNITED STATES PATENT AND TRADEMARK OFFICE
CERTIFICATE OF CORRECTION

PATENT NO. : 6,525,233 B1
DATED : February 25, 2003
INVENTOR(S) : Connor et al.

It is certified that error appears in the above-identified patent and that said Letters Patent is hereby corrected as shown below:

<u>Title page, Item [54] and Column 1, lines 1 and 2,</u>
Title, "PROCESS FOR PREPARING A MODIFIED ALKLARYL" should read
-- PROCESS FOR MAKING SURFACTANTS VIA ADSORPTIVE SEPARATION AND PRODUCTS THEREOF --.

<u>Column 46,</u>
Line 20, "steam" should read -- stream --.

Signed and Sealed this

Twenty-sixth Day of August, 2003

JAMES E. ROGAN
*Director of the United States Patent and Trademark Office*